(12) United States Patent
Yamamoto et al.

(10) Patent No.: US 7,994,159 B2
(45) Date of Patent: Aug. 9, 2011

(54) C-KIT KINASE INHIBITOR

(75) Inventors: Yuji Yamamoto, Tsukuba (JP); Tatsuo Watanabe, Inzai (JP); Masayuki Okada, Tsukuba (JP); Akihiko Tsuruoka, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 1222 days.

(21) Appl. No.: 10/797,903

(22) Filed: Mar. 10, 2004

(65) Prior Publication Data
US 2004/0253205 A1 Dec. 16, 2004

(30) Foreign Application Priority Data

Mar. 10, 2003 (JP) ............... P2003-062823
Aug. 27, 2003 (JP) ............... P2003-302803

(51) Int. Cl.
*A61K 31/33* (2006.01)
*A01N 43/00* (2006.01)

(52) U.S. Cl. ................................... 514/183

(58) Field of Classification Search .............. None
See application file for complete search history.

(56) References Cited

U.S. PATENT DOCUMENTS

| | | | |
|---|---|---|---|
| 4,526,988 A | 7/1985 | Hertel et al. | |
| 4,742,003 A | 5/1988 | Derynck et al. | |
| 5,180,818 A | 1/1993 | Cech et al. | |
| 5,464,826 A | 11/1995 | Grindey et al. | |
| 5,487,889 A | 1/1996 | Eckert et al. | |
| 5,624,937 A | 4/1997 | Reel et al. | |
| 5,656,454 A | 8/1997 | Lee et al. | |
| 5,658,374 A | 8/1997 | Glover | |
| 5,733,913 A | 3/1998 | Blankley et al. | |
| 5,747,651 A | 5/1998 | Lemischka | |
| 5,750,376 A | 5/1998 | Weiss et al. | |
| 5,770,599 A | 6/1998 | Gibson | |
| 5,792,783 A | 8/1998 | Tang et al. | |
| 5,891,996 A | 4/1999 | Mateo de Acosta del Rio et al. | |
| 6,143,764 A | 11/2000 | Kubo et al. | |
| 6,156,522 A | 12/2000 | Keay et al. | |
| 6,217,866 B1 | 4/2001 | Schlessinger et al. | |
| 6,346,398 B1 | 2/2002 | Pavco et al. | |
| 6,476,040 B1 | 11/2002 | Norris et al. | |
| 6,524,583 B1 | 2/2003 | Thorpe et al. | |
| 6,534,535 B1 | 3/2003 | Zhu et al. | |
| 6,676,941 B2 | 1/2004 | Thorpe et al. | |
| 6,797,823 B1 | 9/2004 | Kubo et al. | |
| 6,811,779 B2 | 11/2004 | Rockwell et al. | |
| 6,821,987 B2 | 11/2004 | Kubo et al. | |
| 7,005,430 B2 | 2/2006 | Ueno et al. | |
| 7,135,466 B2 | 11/2006 | Sakai et al. | |
| 7,169,789 B2 | 1/2007 | Kubo et al. | |
| 7,253,286 B2 * | 8/2007 | Funahashi et al. ............ | 546/153 |
| 7,435,590 B2 | 10/2008 | Komurasaki | |
| 7,612,092 B2 | 11/2009 | Funahashi et al. | |
| 7,612,208 B2 | 11/2009 | Matsushima et al. | |
| 2002/0010203 A1 * | 1/2002 | Lipson et al. ................ | 514/418 |
| 2002/0040127 A1 | 4/2002 | Jiang et al. | |
| 2003/0087907 A1 | 5/2003 | Kubo et al. | |
| 2003/0113713 A1 | 6/2003 | Glezer et al. | |
| 2003/0215523 A1 | 11/2003 | Ozawa et al. | |
| 2004/0009965 A1 | 1/2004 | Collins et al. | |
| 2004/0034026 A1 | 2/2004 | Wood et al. | |
| 2004/0053908 A1 | 3/2004 | Funahashi et al. | |
| 2004/0132727 A1 | 7/2004 | Sakai et al. | |
| 2004/0152759 A1 | 8/2004 | Abrams et al. | |
| 2004/0191254 A1 | 9/2004 | Fagin | |
| 2004/0242506 A1 | 12/2004 | Barges Causeret et al. | |
| 2004/0253205 A1 | 12/2004 | Yamamoto et al. | |
| 2005/0014727 A1 | 1/2005 | Muller et al. | |
| 2005/0049264 A1 | 3/2005 | Miwa et al. | |
| 2005/0119303 A1 | 6/2005 | Wakabayashi et al. | |
| 2005/0176802 A1 | 8/2005 | Tang et al. | |
| 2005/0187236 A1 | 8/2005 | Tsuruoka et al. | |

(Continued)

FOREIGN PATENT DOCUMENTS

EP 203126 6/1986

(Continued)

OTHER PUBLICATIONS

Freshney (Culture of Animal Cells, A Manual of Basic Technique, Alan R. Liss., 1983, New York, p. 4.* Dermer (Bio/Technology, 1994, 12: 320).*
Gura (Science, v278, 1997, pp. 1041-1042).*
CancerCare, www.lungcancer.org/reading/types/php, 2009.*
Freshney. Culture of Animal Cells. A manual of basic technique. Alan R. Liss, 1983, New York, p. 4.*
Dermer (Bio/Technology, 1994, 12: 230).*
Sekido et al. Preferential expression of c-kit protooncogene transcripts in small cell lung cancer. Cancer Research, 51, 2416-2419, May 1, 1991.*
Micke et al. Characterization of c-kit expression in small cell lung cancer: prognostic and therapeutic implications. Clinical Cancer Research, vol. 9, 188-194, Jan. 2003.*

(Continued)

*Primary Examiner* — Brandon J Fetterolf
*Assistant Examiner* — Anna Pagonakis
(74) *Attorney, Agent, or Firm* — Fish & Richardson P.C.

(57) ABSTRACT

It was discovered that a compound represented by the general formula (I) shows strong c-Kit kinase inhibitory activity, and it inhibits proliferation of c-Kit kinase activated-cancer cells in vitro and in vivo. A novel anticancer agent showing c-Kit kinase inhibitory activity was discovered.

The general formula (I):

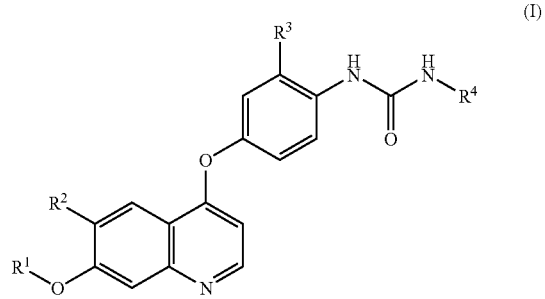

(wherein $R^1$ represents methyl etc., $R^2$ represents cyano etc., $R^3$ represents hydrogen etc., $R^4$ represents hydrogen etc.).

22 Claims, 2 Drawing Sheets

U.S. PATENT DOCUMENTS

| | | |
|---|---|---|
| 2005/0272688 A1 | 12/2005 | Higgins et al. |
| 2005/0277652 A1 | 12/2005 | Matsushima et al. |
| 2006/0004017 A1 | 1/2006 | Stokes et al. |
| 2006/0004029 A1 | 1/2006 | Tsuruoka et al. |
| 2006/0057195 A1 | 3/2006 | Nonomura et al. |
| 2006/0079494 A1 | 4/2006 | Santi et al. |
| 2006/0135486 A1 | 6/2006 | Owa et al. |
| 2007/0004773 A1 | 1/2007 | Sakaguchi et al. |
| 2007/0027318 A1 | 2/2007 | Kubo et al. |
| 2007/0032521 A1* | 2/2007 | Moussy et al. ............... 514/310 |
| 2007/0037849 A1 | 2/2007 | Naito et al. |
| 2007/0078159 A1 | 4/2007 | Matsushima |
| 2007/0117842 A1 | 5/2007 | Arimoto et al. |
| 2008/0214604 A1 | 9/2008 | Furitsu et al. |
| 2009/0047278 A1 | 2/2009 | Owa et al. |
| 2009/0047365 A1 | 2/2009 | Owa et al. |

FOREIGN PATENT DOCUMENTS

| | | |
|---|---|---|
| EP | 0 602 851 | 10/1996 |
| EP | 0 795 556 | 9/1997 |
| EP | 0 837 063 | 4/1998 |
| EP | 0 405 425 | 8/1998 |
| EP | 0 870 842 | 10/1998 |
| EP | 0 684 820 | 8/2001 |
| EP | 1 153 920 | 11/2001 |
| EP | 0712863 | 2/2002 |
| EP | 1 029 853 | 2/2004 |
| EP | 1415987 | 5/2004 |
| EP | 1522540 | 4/2005 |
| EP | 1535910 | 6/2005 |
| EP | 1566379 | 8/2005 |
| EP | 1604665 | 12/2005 |
| EP | 1 683 785 | 7/2006 |
| EP | 1 698 623 | 9/2006 |
| EP | 1698623 | 9/2006 |
| EP | 1859797 | 11/2007 |
| EP | 1925676 | 5/2008 |
| EP | 1925941 | 5/2008 |
| EP | 1949902 | 7/2008 |
| EP | 1964837 | 9/2008 |
| EP | 1 797 881 | 4/2009 |
| GB | 2 253 848 | 9/1992 |
| JP | 63-028427 | 2/1988 |
| JP | 1022874 | 1/1989 |
| JP | 02-291295 | 12/1990 |
| JP | 4341454 | 11/1992 |
| JP | 06-153952 | 6/1994 |
| JP | 7-176103 | 7/1995 |
| JP | 8-045927 | 2/1996 |
| JP | H8-048078 | 2/1996 |
| JP | 09-023885 | 1/1997 |
| JP | 09-234074 | 9/1997 |
| JP | 11-501343 | 2/1999 |
| JP | 11-143429 | 5/1999 |
| JP | 11-158149 | 6/1999 |
| JP | 11-322596 | 11/1999 |
| JP | 3040486 | 3/2000 |
| JP | 3088018 | 7/2000 |
| JP | 2000-328080 | 11/2000 |
| JP | 2001-131071 | 5/2001 |
| JP | 2002-003365 | 1/2002 |
| JP | 2002-114710 | 4/2002 |
| JP | 2002-536414 | 10/2002 |
| JP | 2003-012668 | 1/2003 |
| JP | 2003-026576 | 1/2003 |
| JP | 3420549 | 4/2003 |
| JP | 2003-525595 | 9/2003 |
| JP | 2004-513964 | 5/2004 |
| JP | 2004-155773 | 6/2004 |
| JP | 2004-531549 | 10/2004 |
| JP | 2005-501074 | 1/2005 |
| JP | 2005-504111 | 2/2005 |
| JP | 2005-520834 | 7/2005 |
| JP | 3712393 | 8/2005 |
| JP | 2006-508981 | 3/2006 |
| JP | 2006-515884 | 6/2006 |
| WO | 86/03222 | 6/1986 |
| WO | WO 92/20642 | 11/1992 |
| WO | WO 95/15758 | 6/1995 |
| WO | WO 95/19774 | 7/1995 |
| WO | WO 96/09294 | 3/1996 |
| WO | WO 96/26997 | 9/1996 |
| WO | 96/30347 | 10/1996 |
| WO | 96/33980 | 10/1996 |
| WO | WO 96/39145 | 12/1996 |
| WO | WO 96/40142 | 12/1996 |
| WO | WO 97/03069 | 1/1997 |
| WO | WO 97/13760 | 4/1997 |
| WO | WO 97/13771 | 4/1997 |
| WO | 97/17329 | 5/1997 |
| WO | WO 97/21437 | 6/1997 |
| WO | WO 97/38984 | 10/1997 |
| WO | 97/48693 | 12/1997 |
| WO | WO 98/00134 | 1/1998 |
| WO | WO 98/02434 | 1/1998 |
| WO | WO 98/02437 | 1/1998 |
| WO | WO 98/02438 | 1/1998 |
| WO | 98/14437 | 4/1998 |
| WO | WO 98/13350 | 4/1998 |
| WO | WO 98/23613 | 6/1998 |
| WO | WO 98/32436 | 7/1998 |
| WO | 98/35958 | 8/1998 |
| WO | WO 98/37079 | 8/1998 |
| WO | WO 98/50346 | 11/1998 |
| WO | WO 98/52558 | 11/1998 |
| WO | WO 99/00357 | 1/1999 |
| WO | 99/35146 | 7/1999 |
| WO | WO 99/32106 | 7/1999 |
| WO | WO 99/32110 | 7/1999 |
| WO | WO 99/32111 | 7/1999 |
| WO | WO 99/32436 | 7/1999 |
| WO | WO 99/35132 | 7/1999 |
| WO | WO 99/43654 | 9/1999 |
| WO | 99/62890 | 12/1999 |
| WO | 00/31048 | 6/2000 |
| WO | 00/42012 | 7/2000 |
| WO | 00/43366 | 7/2000 |
| WO | WO 00/42012 | 7/2000 |
| WO | WO 00/43384 | 7/2000 |
| WO | 00/47212 | 8/2000 |
| WO | WO 00/44728 | 8/2000 |
| WO | WO 00/47212 | 8/2000 |
| WO | WO 00/50405 | 8/2000 |
| WO | WO 00/71097 | 11/2000 |
| WO | 01/02369 | 1/2001 |
| WO | 01/23375 | 4/2001 |
| WO | 01/27081 | 4/2001 |
| WO | 01/32926 | 5/2001 |
| WO | WO-01/36403 | 5/2001 |
| WO | 01/40217 | 6/2001 |
| WO | WO 01/45689 | 6/2001 |
| WO | 01/47890 | 7/2001 |
| WO | 01/47931 | 7/2001 |
| WO | 01/60814 | 8/2001 |
| WO | WO 02/16348 | 2/2002 |
| WO | 02/32872 | 4/2002 |
| WO | 02/36117 | 5/2002 |
| WO | 02/41882 | 5/2002 |
| WO | 02/072578 | 9/2002 |
| WO | WO 02/72578 | 9/2002 |
| WO | 02/080975 | 10/2002 |
| WO | 02/088110 | 11/2002 |
| WO | 02/092091 | 11/2002 |
| WO | 03/006462 | 1/2003 |
| WO | WO 03/13529 | 2/2003 |
| WO | WO 03/024386 * | 3/2003 |
| WO | 03/027102 | 4/2003 |
| WO | 03/028711 | 4/2003 |
| WO | 03/033472 | 4/2003 |
| WO | 03/050090 | 6/2003 |
| WO | 03/074045 | 9/2003 |
| WO | 03/079020 | 9/2003 |
| WO | 2004/006862 | 1/2004 |
| WO | 2004/020434 | 3/2004 |
| WO | 2004/032872 | 4/2004 |
| WO | 2004/032937 | 4/2004 |

| WO | WO 2004/035052 | 4/2004 |
| WO | 2004/039782 | 5/2004 |
| WO | 2004/041308 | 5/2004 |
| WO | 2004/043472 | 5/2004 |
| WO | WO 2004/064730 | 8/2004 |
| WO | 2004/078144 | 9/2004 |
| WO | 2004/080462 | 9/2004 |
| WO | WO 2004/080462 | 9/2004 |
| WO | WO 2004/080966 | 9/2004 |
| WO | 2004/101526 | 11/2004 |
| WO | WO 2004/101526 | 11/2004 |
| WO | 2005/027972 | 3/2005 |
| WO | 2005/030140 | 4/2005 |
| WO | 2005/044788 | 5/2005 |
| WO | WO 2005/044788 | 5/2005 |
| WO | 2005/051366 | 6/2005 |
| WO | 2005/056764 | 6/2005 |
| WO | 2005/063713 | 7/2005 |
| WO | WO2005/063713 | 7/2005 |
| WO | 2005/082854 | 9/2005 |
| WO | 2005/092896 | 10/2005 |
| WO | 2005/117887 | 12/2005 |
| WO | 2006/030826 | 3/2006 |
| WO | 2006/030941 | 3/2006 |
| WO | 2006/030947 | 3/2006 |
| WO | WO 2006/030826 | 3/2006 |
| WO | 2006/062984 | 6/2006 |
| WO | 2006/090930 | 8/2006 |
| WO | 2006/090931 | 8/2006 |
| WO | 2006/036941 | 12/2006 |
| WO | 2006/137474 | 12/2006 |
| WO | WO 2006/137474 | 12/2006 |
| WO | 2007/014335 | 2/2007 |
| WO | 2007/015569 | 2/2007 |
| WO | 2007/015578 | 2/2007 |
| WO | 2007/040565 | 4/2007 |
| WO | 2007/052849 | 5/2007 |
| WO | 2007/052850 | 5/2007 |
| WO | 2007/061127 | 5/2007 |
| WO | 2007/061130 | 5/2007 |
| WO | 2007/136103 | 11/2007 |

OTHER PUBLICATIONS

Croom, et al., "Imatinib Mesylate", *Drugs*, 63(5): 513-522, 2003.
Bellone, et al., "Growth Stimulation of Colorectal Carcinoma Cells via the c-kit Receptor is Inhibited by TGF-β-1", *Journal of Cellular Physiology*, 172: 1-11, 1997.
Berdel, et al., "Recombinant Human Stem Cell Factor Stimulates Growth of a Human Glioblastoma Cell Line Expressing c-kit Protooncogene", *Cancer Research*, 52: 3498-3502, 1992.
Bussolino, et al., "Role of Soluble Mediators in Angiogenesis" *Eur. J. Cancer*, 32A(14): 2401-2412, 1996.
Cohen, et al., "Expression of Stem Cell Factor and c-kit in Human Neuroblastoma", *Blood*, 84(10): 3465-3472, 1994.
Deplanque, et al., "Anti-Angiogenic Agents: Clinical Trial Design and Therapies in Development", *European Journal of Cancer*, 36: 1713-1724, 2000.
Folkman, J., "New Perspective in Clinical Oncology From Angiogenesis Research", *Eur J. Cancer*. 32A(14): 2534-2539, 1996.
Folkman, et al., "Angiogenesis", *The Journal of Biological Chemistry*, 267(16): 10931-10934, 1992.
Folkman, et al., "Clinical Applications of Research on Angiogenesis", *The New England Journal of Medicine*, 333(26): 1757-1763, 1995.
Folkman, J., "What is the Evidence that Tumors are Angiogenesis Dependent?", *Journal of the National Cancer Institute*, 82(1): 4-6, 1990.
Furitsu, et al., "Identification of Mutations in the Coding Sequence of the Proto-Oncogene *c-kit* in a Human Mast Cell Leukemia Cell Line Causing Ligand-Independent Activation of *c-kit* Product" *J. Clin. Invest*. 92: 1736-1744, 1993.
Golkar, et al., "Mastocytosis", *Lancet*, 349: 1379-1385, 1997.
Hamel, et al., The Road Less Travelled: *c-kit* and Stem Cell Factor, *Journal of Neuro-Oncology*, 35: 327-333, 1997.
Hibi, et al., "Coexpression of the Stem Cell Factor and the *c-kit* Genes in Small-Cell Lung Cancer", *Oncogene*, 6: 2291-2296, 1991.

Hines, et al., "Coexpression of the c-kit and Stem Cell Factor Genes in Breast Carcinomas", *Cell Growth & Differentiation*, 6: 769-779, 1995.
Hogaboam, et al., "Novel Role of Transmembrane SCF for Mast Cell Activation and Eotaxin Production in Mast Cell-Fibroblast Interactions", *The Journal of Immunology*, 160: 6166-6171, 1998.
Ikeda, et al., "Changes in Phenotype and Proliferative Potential of Human Acute Myeloblastic Leukemia Cells in Culture with Stem Cell Factor", *Experimental Hematology*, 21: 1686-1694, 1993.
Ikeda, et al., "Expression and Functional Role of the Proto-Oncogene *c-kit* in Acute Myeloblastic Leukemia Cells", *Blood*, 78(11): 2962-2968, 1991.
Blume-Jensen, et al., "Activation of the Human *c-kit* Product by Ligand-Induced Dimerization Mediates Circular Actin Reorganization and Chemotaxis", *The EMBO Journal*, 10(13): 4121-4128, 1991.
Kanakura, et al., "Expression, Function and Activation of the Proto-Oncogene c-kit Product in Human Leukemia Cells", *Leukemia and Lymphoma*, 10: 35-41, 1993.
Kay, et al., "Eosinophils and Eosinophil-Associated Cytokines in Allergic Inflammation", *Int. Arch. Allergy Immunol*. 113: 196-199, 1997.
Kitamura, et al., "Regulation of Development, Survival and Neoplastic Growth of Mast Cells through the *c-kit* Receptor", *Int Arch Allergy Immunol*., 107: 54-56, 1995.
Kolibaba, et al., "Protein Tyrosine Kinases and Cancer", *Biochimica et Biophysica Acta*, 1333: F217-F248, 1997.
Kotva, et al., "Substances with Antineoplastic Activity, LIII. N-(δ-(4-Pyrrolo[2,3-d] Pyrimidinylthio) Valeryl} Amino Acids and Analogous Derivatives of Di-and Triglycine", *Collection Czechoslov. Chem. Commun*. 38: 1438-1444, 1973.
Lasota, et al., "Mutations in Exons 9 and 13 of KIT Gene Are Rare Events in Gastrointestinal Stromal Tumors", *American Journal of Pathology*, 157(4): 1091-1095, 2000.
Lev, et al., "A Specific Combination of Substrates is Involved in Signal Transduction by the Kit-Encoded Receptor", *The EMBO Journal*, 10(3): 647-654, 1991.
Longley, et al., "Altered Metabolism of Mast-Cell Growth Factor (c-kit Ligand) in Cutaneous Mastocytosis", *The New England Journal of Medicine*, 328(18): 1302-1307, 1993.
Longley, et al., "Somatic c-KIT Activating Mutation in Urticaria Pigmentosa and Aggressive Mastocytosis: Establishment of Clonality in a Human Mast Cell Neoplasm", *Nature Genetics*, 12: 312-314, 1996.
Lukacs, et al., "Stem Cell Factor (*c-kit* Ligand) Influences Eosinophil Recruitment and Histamine Levels in Allergic Airway Inflammation", *The Journal of Immunology*, 156: 3945-3951, 1996.
Meltzer, E.O., "The Pharmacological Basis for the Treatment of Perennial Allergic Rhinitis and Non-Allergic Rhinitis with Topical Corticosteroids", *Allergy*, 52: 33-40, 1997.
Metcalfe, D., "Classification and Diagnosis of Mastocytosis: Current Status", *J. Invest. Dermatol*, 96: 2S-4S, 1991.
Metcalfe, et al., "Mast Cells", *Physiological Reviews*, 77(4): 1033-1079, 1997.
Metcalf, et al., "Lineage Commitment in the Progeny of Murine Hematopoietic Preprogenitor Cells: Influence of Thrombopoietin and Interleukin 5", *Proc. Nat'l Acad. Sci. USA*, 95: 6408-6412, 1998.
Naclerio, et al., "Rhinitis and Inhalant Allergens", *JAMA*, 278(22): 1842-1848, 1997.
Nagata, et al., "Elevated Expression of the Proto-Oncogene c-kit in Patients with Mastocytosis", *Leukemia*, 12: 175-181, 1998.
Natali, et al., "Breast Cancer is Associated with Loss of the *c-kit* Oncogene Product", *Int. J. Cancer*, 52: 713-717, 1992.
Okayama, et al., "Activation of Eosinophils with Cytokines Produced by Lung Mast Cells", *Int Arch Allergy Immunol*. 114:(suppl 1): 75-77, 1997.
Okayama, et al., "Human Lung Mast Cells are Enriched in the Capacity to Produce Granulocyte-Macrophage Colony-Stimulating Factor in Response to IgE-Dependent Stimulation", *Eur. J. Immunol*. 28: 708-715, 1998.
Scheijen, et al., "Tyrosine Kinase Oncogenes in Normal Hematopoiesis and Hematological Disease", *Oncogene*, 21: 3314-3333, 2002.

Sekido, et al., "Preferential Expression of *c-kit* Protooncogene Transcripts in Small Cell Lung Cancer", *Cancer Research*, 51: 2416-2418, 1991.

Spacey, et al., "Indolocarbazoles, Potent and Selective Inhibitors of Platelet-Derived Growth Factor Receptor Autophosphorylation" *Biochemical Pharmacology*, 55: 261-271, 1998.

Strohmeyer, et al., "Expression of the *hst-1* and *c-kit* Protoonocogenes in Human Testicular Germ Cell Tumors", *Cancer Research*, 51: 1811-1816, 1991.

Taniguchi, et al., "Effect of c-kit Mutation on Prognosis of Gastrointestinal Stromal Tumors", *Cancer Research*, 59: 4297-4300, 1999.

Thomas, et al., "The Eosinophil and its Role in Asthma", *Gen. Pharmac.* 27(4): 593-597, 1996.

Tian, et al., "Activating *c-kit* Gene Mutations in Human Germ Cell Tumors", *American Journal of Pathology*, 154(6): 1643-1647, 1999.

Tonary, et al., "Lack of Expression of c-KIT in Ovarian Cancers is Associated with Poor Prognosis", *Int. J. Cancer (Pred. Oncol)* 89: 242-250, 2000.

Wang, et al., "A Convenient Set of Bidentate Pyridine Ligands for Combinatorial Synthesis", *Tetrahedron Lett.* 40: 4779-4782, 1999.

Wang, et al., "The Expression of the Proto-Oncogene C-Kit in the Blast Cells of Acute Myeloblastic Leukemia", *Leukemia*, 3(10): 699-702, 1989.

International Search Report issued for related PCT application PCT/JP01/09221.

International Search Report issued for related PCT application PCT/JP2004/003087.

Abuzar et al., "Synthesis of some new 7-chloro-4-substituted quinolines as potential antiparasitic agents (1)," *Eur. J. Med. Chem.*, 1986, 21:5-8.

Cairns et al., "New Antiallergic Pyrano[3,2-g]quinoline-2,8-dicarboxylic Acids with Potential for the Topical Treatment of Asthma," *J. Med. Chem.*, 1985, 8(12):1832-1842.

Gall-Istok et al., "Notes on the synthesis of 4-amino-6, 7-di-sec-butoxyquinoline, -6, 7-methylenedioxyquinoline and its N-alkylaminoacetyl derivatives," *Acta Chimica Hungarica*, 1983, 112(2):241-247 (Abstract).

Li et al., "Abrogation of c-*kit*/*Steel factor*-dependent Tumorigenesis by Kinase Defective Mutants of the c-*kit* Receptor: c-*kit* Kinase Defective mutants as Candidate Tools for Cancer Gene Therapy," *Cancer Res.*, 1996, 56:4343-4346.

Nocka et al., "Expression of c-*kit* gene products in known cellular targets of *W* mutations in normal and *W* mutant mice-evidence for an impaired c-*kit* kinase in mutant mice," *Genes Dev.*, 1989, 3:816-826.

Office Action, U.S. Appl. No. 11/347,749 mailed Feb. 9, 2009, 6 pages.

Office Action, Chinese Application No. 200710007097.9, mailed Mar. 6, 2009, 5 pages.

Notice of Allowance, Japanese Application No. P2005-515330, mailed Apr. 21, 2009, 2 pages.

Supplementary European Search Report, EP Application No. 04 71 9054 mailed Apr. 17, 2009, 3 pages.

EP Application No. 06832529.9—European Search Report mailed Jul. 29, 2009 (6 pages).

Heinrich, et al , "Inhibition of c-kit receptor tyrosine kinase activity by STI 571, a selective tyrosine kinase inhibitor," *Blood*, 2000, 96(30); 925-932.

Taguchi, et al., "A novel orally active inhibitor of VEGF receptor tyrosine kinases KRN951: Anti-angiogenic and anti-tumor activity against human solid tumors," *Proc. Amer. Assoc. Cancer. Res.*, 2004, 45: 595.

Myers et al., "The Preparation and SAR of 4-(Anilino), 4-(Phenoxy), and 4-(Thiophenoxy)-Quinazolines: Inhibitors of p56$^{lck}$ and EGF-R Tyrosine Kinase Activity," *Bioorg Med Chem Lett*, 1997, 7(4):417-420.

Nakamura et al., "E7080(ER-203492-00), a Novel VEGF Receptor Tyrosine Kinase Inhibitor-II. Effects on Growth of Human Tumor Xenografts and Life Span of Mice in Colon 38 Orthotopic Transplantation Model," Abstract # 52, *AACR*, Toronto, Canada, Apr. 5-9, 2003.

Nugiel et al., "Synthesis and Evaluation of Indenopyrazoles as Cyclin-Dependent Kinase Inhibitors. 2. Probing the Ideno Ring Substituent Pattern," *J Med Chem*, 2002, 45(24):5224-5232.

Taguchi et al., "A novel orally active inhibitor of VEGF receptor tyrosine kinases KRN951: Anti-angiogenic and anti-tumor activity against human solid tumors," *Proc Am Assoc Cancer Res*, 2004, 45:1070-1071, Abstract 2575.

Takano et al., "Thermal recording materials with improved background stability," Caplus Chemical Abstracts Service, Columbus, Ohio, US, 1996, XP002443195.

Wedge et al., "AZD2171: A Highly Potent, Orally Bioavailable, Vascular Endothelial Growth Factor Receptor-2 Tyrosine Kinase Inhibitor for the Treatment of Cancer," *Cancer Res*, 2005, 65(10):4389-4400.

Yamamoto et al., "E7080 (ER-203492-00), a Novel VEGF Receptor Tyrosine Kinase Inhibitor-III. Significant prolongation of life span in mice transplanted with human ovarian carcinoma based on inhibition of VEGF signaling," Abstract # 50, *AACR*, Toronto, Canada, Apr. 5-9, 2003.

Yamamoto et al., "E7080 a Novel Multitargeted Tyrosine Kinase Inhibitor, has direct anti-tumor efficacy via inhibition of KIT signaling in small cell lung cancer," Abstract #4636, *AACR*, Orlando, FL, Mar. 27-31, 2004.

Yamamoto et al., "E7080 an Oral Multi-Targeted Tyrosine Kinase Inhibitor Has Direct Anti-Tumor Efficacy via Inhibition of KIT Signaling in Gastrointestinal Stromal Tumor (GIST)," Abstract #4038, *97th Annual Meeting AACR*, Washington, DC, Apr. 1-5, 2006.

Supplementary European Search Report in EP 04 81 8213 mailed Jul. 30, 2007, 3 pages.

Notice Requesting Submission of Opinion in Application No. 10-2007-7013993 mailed Jul. 31, 2007, 9 pages (English translation).

Non-Final Office Action in U.S. Appl. No. 10/577,531 mailed Sep. 23, 2008, 17 pages.

Non-Final Office Action in U.S. Appl. No. 10/797,903 mailed Aug. 20, 2009, 12 pages.

Non-Final Office Action in U.S. Appl. No. 10/797,903 mailed Dec. 11, 2007, 12 pages.

Authorized officer Masashi Honda, International Preliminary Report on Patentability in PCT/JP2006/312487 mailed Jan. 10, 2008, 7 pages.

Anderson and Flora, "Preparation of Water-Soluble Compounds Through Salt Formation," *The Practice of Medicinal Chemistry*, 1996, pp. 739-754.

Clark et al., "Safety and Pharmacokinetics of the Dual Action Raf Kinase and Vascular Endothelial Growth Factor Receptor Inhibitor, BAY 43-9006, in Patients with Advanced, Refractory Solid Tumors," *Clin Cancer Res*, 2005, 11(15):5472-5480.

Furitsu and Suzuki, "Stable medicinal compositions of quinolinecarboxamide derivative," Caplus Chemical Abstracts Service, Columbus, Ohio, US, 2006, XP002520305.

Furuta et al., "Synthesis and Biological Evaluation of Selective Inhibitors of PDGF Receptor Auto Phosphorylation," *226$^{th}$ ACS National Meeting*, Sep. 7-11, 2003, New York, NY, Abstract No. 64.

Gardner et al., "In Vitro Activity of Sorghum-Selective Fluorophenyl Urea Herbicides," *Pesticide Biochem Physiol*, 1985, 24(3):285-297.

Haleblian, "Characterization of Habits and Crystalline Modification of Solids and Their Pharmaceutical Applications," *J Pharm Sci*, 1975, 64(8):1269-1288.

Hayek et al., "An In Vivo Model for Study of the Angiogenic Effects of Basic Fibroblast Growth Factor," *Biochem Biophys Res Commun*, 1987, 147(2):876-880.

Jakeman et al., "Developmental Expression of Binding Sites and Messenger Ribonucleic Acid for Vascular Endothelial Growth Factor Suggests a Role for This Protein in Vasculogenesis and Angiogenesis," *Endocrinology*, 1993, 133(2):848-859.

Matsui et al., "E7080(ER-203492-00), a Novel VEGF Receptor Tyrosine Kinase Inhibitor-I. Characterization as an Angiogenesis Inhibitor," Abstract # 51, *AACR*, Toronto, Canada, Apr. 5-9, 2003.

Matsui et al., E7080, a novel inhibitor that targets multiple kinases, has potent antitumor activities against stem cell factor producing human small cell lung cancer H146, based on angiogenesis inhibition, *Int J Cancer*, 2008, 122:664-671.

Matsui et al., "E7080, a Novel Multi-Receptor Tyrosine Kinases Inhibitor, Inhibited in vitro / in vivo VEGF- and SCF-driven Angiogenesis in SCLC Cell Line," Abstract #146, *EORTC-NCI-AACR*, Geneva, Switzerland, Sep. 28-Oct. 1, 2004.

Matsui et al., "Quantitative Analysis of the Profile of Tumor Vessels may be Useful as Predictive Biomarkers for E7080, a KDR Tyrosine Kinase Inhibitor," Abstract #4631, *98th AACR Annual Meeting*, Los Angeles, CA, Apr. 14-18, 2007.

Matsui et al., "VEGFRs inhibitor E7080 inhibits lymph node metastasis of human breast carcinoma, by preventing murine lymphatic endothelial cells from lymphangiogenesis," Abstract # PD12-8, *18th EORTC-NCI-AACR Symposium on Molecular Targets and Cancer Therapeutics*, Prague, Czech Republic, Nov. 7-10, 2006.

Mendel et al., "In Vivo Antitumor Activity of SU11248, a Novel Tyrosine Kinase Inhibitor Targeting Vascular Endothelial Growth Factor and Platelet-derived Growth Factor Receptors: Determination of a Pharmacokinetic/Pharmacodynamic Relationship," *Clin Cancer Res*, 2003, 9:327-337.

Miyazaki et al., "Synthesis, Structure and Biological Activity Relationship of E7080 and its Derivatives as Novel and Potent Antiangiogenic Protein Tyrosine Kinase Inhibitors Including the VEGF Receptors, FGFR1 Receptor and PDGF Receptor," Abstract B-15, *AIMECS03*, Kyoto, Japan, Oct. 14-17, 2003.

European Search Report of EP Application No. 06768437.3, mailed Oct. 17, 2006, 2 pgs.

Office Action of U.S. Appl. No. 11/997,719 dated Sep. 6, 2010, 10 pgs.

Hennequin et al., "Novel 4-Anilinoquinazolines with C-7 Basic Side Chains: Design and Structure Activity Relationship of a Series of Potent, Orally Active, VEGF Receptor Tyrosine Kinase Inhibitors", J. Med Chem. 45:1300-1312, (2002).

Traxler et al., "AEE788: A Dual Family Epidermal Growth Factor Receptor/ErbB2 and Vascular Endothelial Growth Factor Receptor Tyrosine Kinase Inhibitor with Antitumor and Antiangiogenic Activity", Cancer Research, 64:4931-4931 (2004).

[Retrieved from] www.lungcancer/org/reading/types/php, "CancerCare, Types of Lung Cancer" (2009).

Agarwal et al., "Binding of Discoidin Domain Receptor 2 to Collagen I: An Atomic Force Microscopy Investigation", Biochemistry 41:11091-11098 (2002).

Alvares et al., "A Novel Germ-Line Point Mutation in RET Exon 8 (Gly$^{533}$Cys) in a Large Kindred with Familial Medullary Thyroid Carcinoma" The Journal of Clinical Endocrinology & Metabolism 88(11):5438-5443 (2003).

Asuno-Shinyaku, "The New Drugs of Tomorrow", Update Summary Dec. 2006 with English translation (14 pages).

Baker et al., "Blockade of Vascular Endothelial Growth Factor Receptor and Epidermal Growth Factor Receptor Signaling for Therapy of Metastatic Human Pancreatic Cancer", Cancer Research 62: 1996-2003 (2002).

Benjamin et al., "Selective ablation of immature blood vessels in established human tumors follows vascular endothelial growth factor withdrawal", The J. of Clin. Invest. 103(2):159-165 (1999).

Bergers et al., "Benefits of targeting both pericytes and endothelial cells in the tumor vasculature with kinase inhibitors", The Journal of Clinical Investigation 111(9):1287-1295 (2003).

Bruns et al., "Effect of the Vascular Endothelial Growth Factor Receptor-2 Antibody DC101 Plus Gemcitabine on Growth, Metastasis and Angiogenesis of Human Pancreatic Cancer Growing Orthotopically in Nude Mice", Int. J. Cancer 102:101-108 (2002).

Capellen et al., "Frequent activating mutations of FGFR3 in human bladder and cervix carcinomas", Nature Genetics, 23:18-20 (1999).

Carlomagno et al., "ZD6474, an Orally Available Inhibitor of KDR Tyrosine Kinase Activity, Efficiently Block Oncogenic RET Kinases", Cancer Research 62:7284-7290(2002).

Carlomagno et al., "BAY 43-9006 Inhibition of Oncogenic RET Mutants", Journal of the National Cancer Institute 98(5):326-334 (2006).

Chen et al., "FGFR3 as a therapeutic target of the small molecule inhibitor PKC412 in hematopoietic malignancies", Oncogene 24:8259-8267 (2005).

Chesi et al., "Activated fibroblast growth factor receptor 3 is an oncogene that contributes to tumor progression in multiple myeloma", Neoplasia, Blood, 97(3):729-736 (2001).

Chesi et al., "Frequent translocation t(4;14)(p16.3;q32.3) in multiple myeloma is associated with increased expression and activating mutations of fibroblast growth factor receptor", Nature Genetics, 16:260-264 (1997).

Elisei et al., "Identification of a Novel Point Mutation in the RET Gene (Ala883Thr), Which Is Associated with Medullary Thyroid Carcinoma Phenotype Only in Homozygous Condition", The Journal of Clinical Endocrinology & Metabolism 89(11):5823-5827 (2004).

Erber et al., "Combined inhibition ofVEGF- and PDGF-signaling enforces tumor vessel regression by interfering with pericytemediated endothelial cell survival mechanisms", The FASEB Journal published online Dec. 4, 2003 (25 pages).

Experimental and Molecular Therapeutices 30, Proceedings of the American Association for Cancer Research, vol. 47 (2006).

Gatzemeier et al., "Phase III Comparative Study of High-Dose Cisplatin Versus a Combination of Paclitaxel and Cisplatin in Patients With Advanced Non-Small-Cell Lung Cancer", Journal of Clinical Oncology 18(19):3390-3399 (2000).

Giles, F., "The Vascular Endothelial Growth Factor (VEGF) Signaling Pathway: A Therapeutic Target in Patients with Hematologic Malignancies", The Oncologists 6(suppl5):32-39 (2001).

Haller, D., "Chemotherapy for Advanced Pancreatic Cancer", Int. J. Radiation Oncology Biol. Phys., 56(4): Supplement, pp. 16-23 (2003).

Hattori et al., "Immunohistochemical Detection of K-sam Protein in Stomach Cancer", Clinical Cancer Research, 2:1373-1381 (1996).

Haymo et al., "Pericytes in experimental MDA-MB231 tumor angiogenesis", Histochemistry and Cell Biology, 117(6):527-534 (2002).

Heinrich et al., "Inhibition of c-kit receptor tyrosine kinase activity by STI 571, a selective tyrosine kinase inhibitor", Hematopoiesis, Blood 96(3):925-932 (2000).

Heinrich et al., "Inhibition of KIT Tyrosine Kinase Activity: A Novel Molecular Approach to the Treatment of KIT-Positive Malignancies", Journal of Oncology 20(6):1692-1703 (2002).

Hurwitz et al., "Bevacizumab plus Irinotecan, Fluorouracil, and Leucovorin for Metastatic Colorectal Cancer", The New England Journal of Medicine, 350(23):2335-2342 (2004).

Inai et al., "Inhibition of Vascular Endothelial Growth Factor (VEGF) Signaling in Cancer Causes Loss of Endothelial Fenestrations, Regression of Tumor Vessels, and Appearance of Basement Membrane Ghosts", American J. of Pathol. 165(1): 35-52 (2004).

Inoue et al., "Molecular Target Therapy Targeting Angiogenesis Pathways", The Nishinihon J. Urol., 66:425-432 (2004).

Itoh et al., "Preferential Alternative Splicing in Cancer Generates a K-sam Messenger RNA with Higher Transforming Activity", Cancer Research 54: 3237-3241(1994).

Jhiang, S., "The RET proto-oncogene in human cancers", Oncogene 19:5590-5597 (2000).

Jimenez et al., "Pheochromocytoma and Medullary Thyroid Carcinoma:A New Genotype-Phenotype Correlation of the *RET* Protooncogene 891 Germline Mutation", The Journal of Clinical Endocrinology & Metabolism 89(8):4142-4145 (2004).

Johnson et al., "Paclitaxel Plus Carboplatin in Advanced Non-Small-Cell Lung Cancer: A Phase II Trial", Journal of Clinical Oncology 14(7):2054-2060 (1996).

JP Journal of Cancer and Chemotherapy, 21(14): 2398-2406 (1994).

JP Journal of Cancer and Chemotherapy, 31(7):1093-1095 (2004).

Jung et al., "Effects of combination anti-vascular endothelial growth factor receptor and anti-epidermal growth factor receptor therapies on the growth of gastric cancer in a nude mouse model", European Journal of Cancer, 38:1133-1140 (2002).

Kashuk et al., "Phenotype-genotype correlation in Hirschsprung disease is illuminated by comparative analysis of the RET protein sequence", PNAS 102(25):8949-8954 (2005).

Kelly et al., "Randomized Phase III Trial of Paclitaxel Plus Carboplatin Versus Vinorelbine Plus Cisplatin in the Treatment of Patients With Advanced Non-Small-Cell Lung Cancer: A Southwest Oncology Group Trial", Journal of Clinical Oncology 19(13):3210-3218 (2001).

Kim et al., "A Phase II Study of Irinotecan Plus Cisplatin for Patients With Advanced Stage IIIB or IV NSCLC Previously Treated With Nonplatinum-Based Chemotherapy", Cancer, 107(4):799-805 (2006).

Kim et al., "An Orally Administered Multitarget Tyrosine Kinase Inhibitor, SU11248, Is a Novel Potent Inhibitor of Thyroid Oncogenic RET/Papillary Thyroid Cancer Kinases", The Journal of Clinical Endocrinology & Metabolism 91(10):4070-4075 (2006).

Lesueur et al., "Polymorphisms in RET and Its Coreceptors and Ligands as Genetic Modifiers of Multiple Endocrine Neoplasia Type 2A", Cancer Research 66(2):1177-1180 (2006).

Lin et al., "The Vascular Endothelias Growth Factor Receptor Tyrosine Kinase Inhibitor PTK787/ZK222584 Inhibits Growth and Migration of Mutiple Myeloma Cells in the Bone Marrow Microenvironment", Cancer Research, 62:5019-5026 (2002).

Logie et al., "Activating mutations of the tyrosine kinase receptor FGFR3 are associated with benign skin tumors in mice and humans", Human Molecular Genetics, 14(9):1153-1160 (2005).

Matsui et al., "146 E7080, a novel multi-targeted tyrosine kinase inhibitor, exhibits anti-angiogenic activity via inhibition of KIT signaling in a small cell lung cancer xenograft model", European Journal of Cancer, Supplement Pergamon, Oxford, GB XP004639590 abstract.

McCarty et al., "ZD6474, a vascular endothelial growth factor receptor tyrosine kinase inhibitor with additional activity against epidermal growth factor receptor tyrosine kinase, inhibits orthotopic growth and angiogenesis of gastric cancer", Molecular Cancer Therapeutics, 3(9):1041-1048 (2004).

McCulloch et al., "*Astragalus*-Based Chinese Herbs and Platinum-Based Chemotherapy for Advanced Non-Small-Cell Lung Cancer: Meta-Analysis of Randomized Trials", Journal of Clinical Oncology 24(3):419-430 (2006).

Miller et al., "Paclitaxel plus Bevacizumab versus Paclitaxel Alone for Metastatic Breast Cancer", The New England Journal of Medicine, 357(26):2666-76 (2007).

Mologni et al., "Inhibition of RET tyrosine kinase by SU5416", Journal of Mol. Endo., 37:199-212 (2006).

Morgan et al., "Dynamic Contrast-Enhanced Magnetic Resonance Imaging As a Biomarker for the Pharmacological Response of PTK787/ZK 222584, an Inhibitor of the Vascular Endothelial Growth Factor Receptor Tyrosine Kinases, in Patients With Advanced Colorectal Cancer and Liver Metastases: Results From Two Phase I Studies", Journal of Oncology 21(21):3955-3964 (2003).

Morikawa et al., Angiogenesis and Pericytes, Putative Positive Function of Pericytes in Angiogenesis, Course of Cellular Biology, with English translation, Cell, 37(4):164-168 (2005).

Naski et al., "Graded activation of fibroblast growth factor receptor 3 by mutations causing achondroplasia and thanatophoric dysplasia", Nature Genetics 13:233-237 (1996).

Ohe et al., "Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan", Annals of Oncology 18:317-323 (2007).

Olaso et al., "DDR2 receptor promotes MMP-2-mediated proliferation and invasion by hepatic stellate cells", The Journal of Clinical Investigation, 108( 9):1369-1378 (2001).

Ozols et al., "Phase III Trial of Carboplatin and Paclitaxel Compared With Cisplatin and Paclitaxel in Patients With Optimally Resected Stage III Ovarian Cancer: A Gynecologic Oncology Group Study", Journal of Oncology 21(17):3194-3200 (2003).

Paterson et al., "Preclinical studies of fibroblast growth factor receptor 3 as a therapeutic target in multiple myeloma", Blackwell Publishing Ltd, British Journal of Haematology, 124: 595-603 (2004).

Plowright et al., "Ectopic expression of fibroblast growth factor receptor 3 promotes myeloma cell proliferation and prevents apoptosis" Neoplasia, Blood, 95(3): 992-998 (2000).

Salmon et al., "Anti-Angiogenic Treatment of Gastrointestinal Malignancies", New Drugs, Cancer Investigation 23:712-726 (2005).

Sandler et al., "Phase III Trial of Gemcitabine Plus Cisplatin Versus Cisplatin Alone in Patients With Locally Advanced or Metastatic Non-Small-Cell Lung Cancer", Journal of Clinical Oncology 18(1):122-130 (2000).

Santoro et al., "Drug Insight: small-molecule inhibitors of protein kinases in the treatment of thyroid cancer", Nature Clinical Practice Endocrinology & Metabolism 2(1):42-52 (2006).

Santoro et al., "Minireview: RET: Normal and Abnormal Functions", Endocrinology 145(12):5448-5451 (2004).

Shiang et al., "Mutations in the Transmembrane Domain of FGFR3 Cause the Most Common Genetic Form of Dwarfism, Achondroplasia", Cell 78:335-342 (1994).

Shimizu et al., "Orally active anti-proliferation agents: novel diphenylamine derivatives as FGF-R2 autophosphorylation inhibitors", Bioorganic & Medicinal Chem. Letters 14:875-879 (2004).

Tan et al., "Randomized study of vinorelbine-gemcitabine versus vinorelbine-carboplatin in patients with advanced non-small cell lung cancer", Lung Cancer, 49:233-240 (2005).

Trudel et al., "Inhibition of fibroblast growth factor receptor 3 induces differentiation and apoptosis in t(4;14) myeloma", Neoplasia, Blood, 103(9): 3521-3528 (2004).

Trudel et al., "CHIR-258, a novel, multitargeted tyrosine kinase inhibitor for the potential treatment of t(4;14) multiple myeloma", Neoplasia, Blood 105(7):2941-2948 (2005).

Ueda et al., "Deletion of the Carboxyl-Terminal Exons of K-sam/FGFR2 by Short Homology-mediated Recombination, Generating Preferential Expression of Specific Messenger RNAs", Cancer Research, 59:6080-6086 (1999).

Van Oers et al., "A Simple and Fast Method for the Simultaneous Detection of Nine Fibroblast Growth Factor Receptor 3Mutations in Bladder Cancer and Voided Urine", Clin Cancer Res 11(21):7743-7748 (2005).

Vogel et al., "Sensing extracellular matrix: An update on discoidin domain receptor function", Cellular Signalling 18:1108-1116 (2006).

Wang et al., "Phase II study of gemcitabine and carboplatin in patients with advanced non-small-cell lung cancer", Cancer Chemother Pharmacol, 60:601-607 (2007).

Werner et al., "Gastric adenocarcinoma: pathormorphology and molecular pathology", J. Cancer Res. Clin. Oncol. 127:207-216 (2001).

Willett et al., "Direct evidence that the VEGF-specific antibody bevacizumab has antivascular effects in human rectal cancer", Nature Medicine 10(2):145-147 (2004).

Wozniak et al., "Randomized Trial Comparing Cisplatin With Cisplathn Plus Vinorelbine in the Treatment of Advanced Non-Small•Cell Lung. Cancer: A Southwest Oncology Group Study", Journal of Clinical Oncology 16(7):2459-2465 (1998).

Yamada et al., "New Technique for Staining", Monthly Medical Technology, (1999), (13 pgs).

Yanagihara et al., "Development and biological analysis of peritoneal metastasis mouse models for human scirrhous stomach cancer", Cancer Sci, 96(6):323-332 (2005).

Zhu et al., "Fibroblast growth factor receptor 3 inhibition by short hairpin RNAs leads to apoptosis in multiple myeloma", Mol Cancer Ther 4(5):787-798 (2005).

Zieger et al., "Role of Activating Fibroblast Growth Factor Receptor 3 Mutations in the Development of Bladder Tumors", Clin Cancer Res 11(21):7709-7719 (2005).

Office Action dated Oct. 30, 2009 for European Application No. 04719054.1, (5 pgs).

Office Action dated Aug. 20, 2009 for U.S. Appl. No. 10/797,903, (10 pgs).

European Search Report dated May 7, 2010 for European Application No. 07743994, (9pgs).

European Search Report dated Jul. 23, 2010 for European Application No. 06782407, (8 pgs).

International Search report dated Sep. 5, 2006 for International Application No. PCT/JP2006/315563, (2 pgs).

International Search report dated Nov. 17, 2006 for International Application No. PCT/JP2006/315698, (5 pgs).

International Search report dated Jan. 23, 2007 for International Application No. PCT/JP2006/322514, (10 pgs).

International Search report dated Jan. 23, 2007 for International Application No. PCT/JP2006/323881, (6 pgs).
International Search report dated Sep. 11, 2007 for International Application No. PCT/JP2007/060560, (6 pgs).
International Search report dated Sep. 4, 2007 for International Application No. PCT/JP2007/063525, (7 pgs).
International Search report and Written Opinion dated Sep. 14, 2010 for International Application No. PCT/JP2010/063804, (10 pgs).
International Search report dated Nov. 20, 2007 for International Application No. PCT/JP2007/067088, (6 pgs).
International Search report dated Apr. 1, 2008 for International Application No. PCT/JP2008/051024, (6 pgs).
International Search report dated Mary 4, 2008 for International Application No. PCT/JP2008/051697, (7 pgs).
International Search report dated Jan. 20, 2009 for International Application No. PCT/JP2008/070321, (8 pgs).
International Search report dated Mar. 24, 2009 for International Application No. PCT/JP2009/051244, (6 pgs).

* cited by examiner

COMPOUND 1    0    0    0.1    0.3    1    3    10    30    100 nM

SCF(50ng/ml)

C-KIT KINASE INHIBITOR

BACKGROUND OF THE INVENTION

Priority Information

This application claims priority benefits under 35 U.S.C. § 119 to Japanese Patent Application No. P2003-062823, filed Mar. 10, 2003, and to Japanese Patent Application No. P2003-302803, filed on Aug. 27, 2003. The entire teachings of the above applications are incorporated herein by reference.

1. Field of the Invention

The present invention relates to a c-Kit kinase inhibitor, a therapeutic agent for a disease caused by the excessive activation of c-Kit kinase comprising c-Kit kinase inhibitor as an active ingredient.

2. Related Background of the Invention

Intracellular signal transduction by receptor tyrosine kinase contributes to cell proliferation, differentiation and metabolism; as a result, it is responsible for various diseases including cancers (Kolibaba K. S. et al., B.B.A. 1333, F217-F248, 1997; and Sheijen B. et al. Oncogene 21, 3314-3333, 2002).

c-Kit kinase, one of receptor tyrosine kinase, binds to SCF (stem cell factor) which is a ligand specific for the kinase. This causes dimerization of the kinase itself and the subsequent activation of the kinase activity. Consequently, a variety of substrates of c-Kit kinase in cells will be phosphorylated (Blume-Jensen P. et al., EMBO J. 10, 4121-4128, 1991; and Lev S. et al., EMBO J., 10, 647-654, 1991).

The abnormal activation of c-Kit kinase generates a proliferation signal in certain types of cancer cells (their representatives are described below), which is regarded as the cause of cancerization or malignant transformation.

(1) Acute myelogenous leukemia (AML): The expression of c-Kit kinase was found in a number of patients (60-80%) suffering from acute myelogenous leukemia and the proliferation of blast derived from the patients was stimulated by SCF. Furthermore, in 13 out of 18 patients the activation of c-Kit kinase was observed without SCF stimulation. It was then thought that activating mutations of c-Kit kinase occurred in these patients (Lev S. et al., EMBO J., 10, 647-654, 1991; Wang C et al., Leukemia 3, 699-702, 1989; Kanakura Y. et al., Leuk. Lymph. 10, 35-41, 1993; Ikeda H. et al., Blood, 78, 2962-2968, 1991; and Ikeda H. et al., Exp. Hematol. 21, 1686-1694, 1993).

(2) Mast cell leukemia: There was a report that activating mutations of c-Kit kinase was found in the cell line of mast cell leukemia a mastocytosis patient had developed (Furitsu T. et al., J. Clin. Invest., 92, 1736-1744, 1993).

(3) Small cell lung cancer (SCLC): While high level expression of c-Kit kinase was observed in more than 70% of SCLC cell lines, the expression levels of c-Kit kinase in the cell lines of non-small cell lung cancers were either low or below the detection limit. SCF, a ligand for c-Kit kinase, is also expressed in the cell lines of SCLC. This suggested the possibility that autocrine proliferation was promoted (Hibi K. et al., Oncogene, 6, 2291-2296, 1991; and Sekido Y. et al., Cancer Res., 51, 2416-2419, 1991).

(4) GIST (gastrointestinal stromal tumors): GIST is defined as a stromal tumor that develops in the GI tract expressing c-Kit kinase. In about a half of GIST, activating mutations of c-Kit kinase was found and it was present at high frequency in GIST with high malignancy. This suggested the possibility of the mutation being a prognosis factor (Lasota J. et al., Am. J. Pathol., 157, 1091-1095, 2000; and Taniguchi M. et al., Cancer Res., 59, 4297-4300, 1999).

(5) Testicular cancer: In testicular cancer, carcinoma in situ (CIS), which is regarded as a precancerous lesion, progresses to form tumors which are referred to as "seminoma" and "non-seminoma." High-level expression of c-Kit kinase in CIS and seminoma was reported (Stromeyer T. et al., Cancer Res., 51, 1811-1816, 1991). In recent years there has been a report on the expression of c-Kit kinase that underwent an activating mutation in seminoma (Tian Q. et al., Am. J. Pathol., 154, 1643-1647, 1999).

(6) Ovarian cancer: There has been reported as follows. In normal ovarian epithelia, SCF was expressed but the expression of c-Kit kinase was not observed. However, c-Kit kinase and SCF were both expressed in benign ovarian tumor at an early stage of cancerization; oppositely, the expression of c-Kit kinase was lowered in malignant ovarian tumor. These results suggested that c-Kit kinase played an important role in the development of ovarian cancer (Tonary A. T., Int. J. Cancer, 89, 242-250, 2000).

(7) Breast cancer: There was a report that the expression of c-Kit kinase was lowered in breast cancer as compared to the surrounding normal tissues (Natali P. et al., Int. J. Cancer, 52, 713-717, 1992). However, in later studies the expression of c-Kit kinase, which had not been detected in normal tissue, was observed in breast cancer and SCF expression was also detected. These suggested that the autocrine stimulation promoted proliferation (Hines S. J. et al., Cell Growth & Differentiation, 6, 769-779, 1995).

(8) Brain cancer: There has been reported as follows: c-Kit kinase expression was observed in the cell line and tissue of glioblastoma that had the highest level of malignancy among brain cancers; and in the glioblastoma cell line expressing c-Kit kinase SCF stimulation promoted growth (Berdel W. E. et al., Cancer Res., 52, 3498-3502, 1992).

(9) Neuroblastoma: There has been reported as follows. SCF and c-Kit kinase were coexpressed in many cases of the cell lines and the tissue specimens of neuroblastoma which was well known as the cancer that developed in infants. Anti-c-Kit kinase antibody suppressed the growth of the cell line of neuroblastoma, and thus, growth was promoted by an autocrine mechanism (Cohen P. S., Blood, 84, 3465-3472, 1994).

(10) Colorectal cancer: Coexpression of c-Kit kinase and its ligand, SCF, was observed in a colorectal cancer tissue, whereas the expression of neither one was observed in a normal mucosal tissue. SCF stimulation promoted proliferation of the colorectal cancer cell line (Bellone G. et al., J. Cell. Physiol., 172, 1-11, 1997).

It was reported that the activation of c-Kit kinase by SCF stimulation was essential to proliferation and differentiation of mast cells (Hamel et al., J. Neuro-Onc., 35, 327-333, 1997; and Kitamura et al., Int. Arch. Aller. Immunol., 107, 54-56, 1995). It has, therefore, been thought that the excessive activation of c-Kit kinase is responsible for immunological abnormalities (such as mastocytosis, asthma and chronic rhinitis) which are caused by the excessive mast cells.

(1) Mastocytosis: Mastocytosis is a general term for the pathology of various conditions characterized by the excessive growth of mast cells (Metcalf, J. Invest. Derm. 93, 2S-4S, 1991; and Golkar et al., Lancet, 349, 1379-1385, 1997). The following have been reported on mastocytosis patients: 1) the excessive expression of c-Kit kinase (Nagata et al., Mastocytosis Leuk., 12, 175-181, 1998); 2) an increase in the amount of soluble SCF (Longley et al., New Engl. J. Med., 328, 1302-1307, 1993); and 3) activating mutations of c-Kit kinase (Nagata et al., Mastocytosis Leuk., 12, 175-181, 1998; and Longley et al., Nat. Gen., 12, 312-314, 1996). These are believed to excessively activate c-Kit kinase and thus to cause mastocytosis.

(2) Allergy and asthma: Mast cells and eosinophils are important cells in the development of inflammation, allergy, asthma and the like (Thomas et al., Gen. Pharmacol., 27, 593-597, 1996; and Metcalf et al., Physiol. Rev., 77, 1033-1079, 1997). This is suggested by the report that corticosteroids which are currently believed to be most effective against inflammations involving chronic rhinitis or allergy decrease the numbers of circuiting and invading mast cells and eosinophils (Naclerio et al., JAMA, 278, 1842-1848, 1997; and Meltzer, Aller., 52, 33-40, 1997). The activation of c-Kit kinase resulting from SCF stimulation was not only essential to differentiation, survival and proliferation of mast cells, but also promoted the induction of various factors from the mast cells. These factors fulfilled an important function in differentiation, survival and invasiveness of the eosinophils (Okayama et al., Int. Arch. Aller. Immunol., 114, 75-77, 1997; Okayama et al., Eur. J. Immunol., 28, 708-715, 1998; Metcalf et al., Proc. Natl. Acad. Sci., 95, 6408-6421, 1998; Kay et al., Int. Arch. Aller. Immunol., 113, 196-199, 1997; Hogaboam et al., J. Immunol. 160, 6166-6171, 1998; and Luckas et al., J. Immunol. 156, 3945-3951, 1996). It has, therefore, been thought that the inhibition of c-Kit kinase can suppress the activated mast cells and eosinophils in the patients suffering from asthma or allergy.

As stated above, c-Kit kinase is believed to be closely involved in the development or the malignant transformation of some types of cancers as well as in the diseases for which excessive mast cells are regarded as the cause. Inhibitors of c-Kit kinase have been considered useful as therapeutic agents for those diseases.

SUMMARY OF THE INVENTION

The problem to be solved by the invention is to discover a novel compounds exhibiting c-Kit kinase inhibitory activity and to develop a therapeutic agent for diseases caused by c-Kit kinase.

Compounds having an indoline skeleton were reported as those showing c-Kit kinase inhibitory action (WO 01/45689). There was also a report concerning the inhibitory action on c-Kit kinase by the compounds having a quinazoline skeleton (WO 01/47890). An analogue (KRN633) was also reported to possess c-Kit kinase inhibitory action (Kazuo Kubo et al., 22nd Symposium on Medicinal Chemistry, Abstracts, pp. 275-277, 2P-320, 2002). Recently, Gleevec (STI571) was approved in U.S., Europe and Japan as a therapeutic agent for GIST based on c-Kit inhibition (Drugs, 63: 513-22, 2003).

We have reported that a compound represented by the following general formula (I) inhibits kinase activity of VEGF receptor, and that it also inhibits tube formation of vascular endothelial cells stimulated by VEGF, FGF2 or HGF (WO02/32872) And, we discovered that a compound represented by the following general formula (I) inhibits not only VEGF kinase but also c-Kit kinase, and that it has an inhibitory activity against proliferation of cancer cells expressing c-Kit kinase.

Specifically, the invention relates to:
<1> A c-Kit kinase inhibitor comprising as an active ingredient, a compound represented by the general formula (I), a salt thereof or a hydrate of the foregoing:

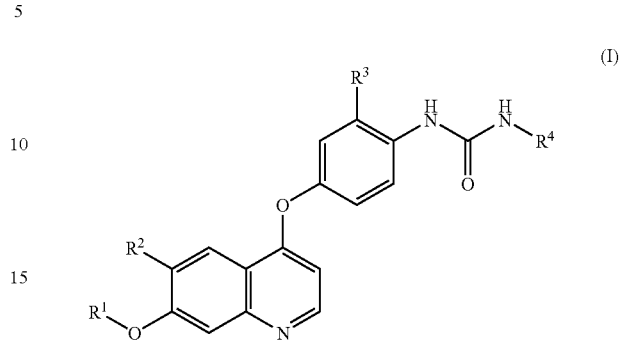

(wherein $R^1$ represents methyl, 2-methoxyethyl or a group represented by the formula (II):

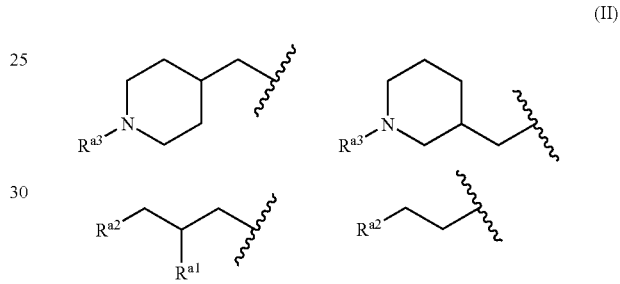

(wherein $R^{a3}$ represents methyl, cyclopropylmethyl or cyanomethyl; $R^{a1}$ represents hydrogen, fluorine or hydroxyl; and $R^{a2}$ represents 1-pyrrolydinyl, 1-piperidinyl, 4-morpholinyl, dimethylamino or diethylamino);

$R^2$ represents cyano or —CONHR$^{a4}$ (wherein R$^{a4}$ represents hydrogen, $C_{1-6}$ alkyl, $C_{3-8}$ cycloalkyl, $C_{1-6}$ alkoxy or $C_{3-8}$ cycloalkoxy);

$R^3$ represents hydrogen, methyl, trifluoromethyl, chlorine or fluorine; and $R^4$ represents hydrogen, methyl, ethyl, n-propyl, cyclopropyl, 2-thiazolyl or 4-fluorophenyl).

<2> The c-Kit kinase inhibitor according to <1>, wherein $R^1$ represents methyl.

<3> The c-Kit kinase inhibitor according to <1>, wherein $R^4$ represents methyl, ethyl or cyclopropyl.

<4> The c-Kit kinase inhibitor according to <1>, wherein $R^3$ represents hydrogen, chlorine or fluorine.

<5> The c-Kit kinase inhibitor according to <1>, wherein $R^2$ represents —CONHR$^{a4}$ (wherein R$^{a4}$ represents hydrogen or methoxy).

<6> The c-Kit kinase inhibitor according to <1>, wherein the compound represented by the general formula (I) is a compound selected from the group consisting of 4-(3-chloro-4-(cyclopropylaminocarbonyl)aminophenoxy)-7-methoxy-6-quinolinecarboxamide, 4-(3-chloro-4-(ethylaminocarbonyl)aminophenoxy)-7-methoxy-6-quinolinecarboxamide, N6-methoxy-4-(3-chloro-4-(((cyclopropylamino)carbonyl) amino)phenoxy)-7-methoxy-6-quinolinecarboxamide and N6-methoxy-4-(3-chloro-4-(((ethylamino)carbonyl)amino) phenoxy)-7-methoxy-6-quinolinecarboxamide.

<7> An anticancer agent for treating a cancer expressing excessive c-Kit kinase or a mutant c-Kit kinase, comprising as an active ingredient, the c-Kit kinase inhibitor according to <1>.

<8> The anticancer agent according to <7>, wherein the cancer expressing excessive c-Kit kinase or a mutant c-Kit kinase is acute myelogenous leukemia, mast cell leukemia, a small cell lung cancer, GIST, a testicular cancer, an ovarian cancer, a breast cancer, a brain cancer, neuroblastoma or a colorectal cancer.

<9> The anticancer agent according to <7>, wherein the cancer expressing excessive c-Kit kinase or a mutant c-Kit kinase is acute myelogenous leukemia, a small cell lung cancer or GIST.

<10> The anticancer agent according to <7>, which is applied to a patient for which a cancer expressing excessive c-Kit kinase or a mutant c-Kit kinase is identified.

<11> A therapeutic agent for mastocytosis, allergy or asthma, comprising as an active ingredient, the c-Kit kinase inhibitor according to <1>.

<12> A therapeutic method for a cancer, comprising administering to a patient suffering from a cancer expressing excessive c-Kit kinase or a mutant c-Kit kinase, a pharmacologically effective dose of the c-Kit kinase inhibitor according to <1>.

<13> The method according to <12>, wherein the cancer expressing excessive c-Kit kinase or a mutant c-Kit kinase is acute myelogenous leukemia, mast cell leukemia, a small cell lung cancer, GIST, a testicular cancer, an ovarian cancer, a breast cancer, a brain cancer, neuroblastoma or a colorectal cancer.

<14> The method according to <12>, wherein the cancer expressing excessive c-Kit kinase or a mutant c-Kit kinase is acute myelogenous leukemia, a small cell lung cancer or GIST.

<15> A therapeutic method for a cancer, comprising the steps of:
extracting cancer cells from a patient suffering from a cancer;
confirming that the cancer cells are expressing excessive c-Kit kinase or a mutant c-Kit kinase; and administering to the patient a pharmacologically effective dose of the c-Kit kinase inhibitor according to <1>.

<16> A therapeutic method for mastocytosis, allergy or asthma, comprising administering to a patient suffering from the disease, a pharmacologically effective dose of the c-Kit kinase inhibitor according to <1>.

<17> A method for inhibiting the c-Kit kinase activity, comprising applying to a cell expressing excessive c-Kit kinase or a mutant c-Kit kinase, a pharmacologically effective dose of the c-Kit kinase inhibitor according to <1>.

A compound showing a strong c-Kit kinase inhibitory activity has been discovered, a therapeutic agent for suppressing cancerization and malignant transformation of certain kind of cancer, or a therapeutic agent for diseases considered to be caused by c-kit kinase, such as mastocytosis, allergy or asthma can be provided.

DESCRIPTION OF THE PREFERRED EMBODIMENTS

Figure 1:
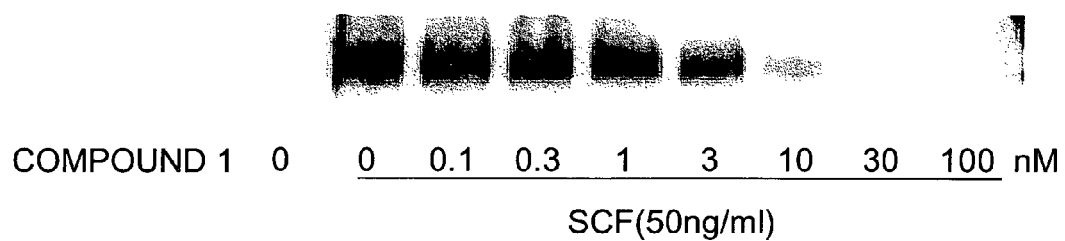
FIG. 1 is a graph showing the results of immunoblot of phosphorylated c-Kit kinase by SCF stimulation.

The embodiments of the present invention will be explained below.

Several of the structural formulas given for compounds throughout the present specification will represent a specific isomer for convenience, but the invention is not limited to such specific isomers and encompasses all isomers and isomer mixtures, including geometric isomers, asymmetric carbon-derived optical isomers, stereoisomers and tautomers, implied by the structures of the compounds. Moreover, the compounds of the invention also include those that have been metabolized in the body by oxidation, reduction, hydrolysis, conjugation or the like, and still exhibit the desired activity, while the invention further encompasses all compounds which undergo metabolism such as oxidation, reduction, hydrolysis, etc. in the body to produce the compounds of the invention. Solvates, including those with water, are also encompassed by the invention.

The term "$C_{1-6}$ alkyl" as used throughout the present specification refers to linear or branched alkyl of 1 to 6 carbons, and as specific examples there may be mentioned methyl, ethyl, n-propyl, i-propyl, n-butyl, i-butyl, sec-butyl, t-butyl, n-pentyl, i-pentyl, sec-pentyl, t-pentyl, neopentyl, 1-methylbutyl, 2-methylbutyl, 1,1-dimethylpropyl, 1,2-dimethylpropyl, n-hexyl, i-hexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably methyl, ethyl, n-propyl, i-propyl, n-butyl, i-butyl, sec-butyl, t-butyl, n-pentyl, i-pentyl, sec-pentyl, t-pentyl, neopentyl, 1-methylbutyl, 2-methylbutyl, 1,1-dimethylpropyl, 1,2-dimethylpropyl, n-hexyl and i-hexyl, more preferably methyl, ethyl, n-propyl, i-propyl, n-butyl, i-butyl, sec-butyl, t-butyl, n-pentyl, i-pentyl, sec-pentyl, t-pentyl, neopentyl, 1-methylbutyl, 2-methylbutyl, 1,1-dimethylpropyl and 1,2-dimethylpropyl, even more preferably methyl, ethyl, n-propyl, i-propyl, n-butyl, i-butyl, sec-butyl and t-butyl, and most preferably methyl, ethyl, n-propyl and i-propyl.

The term "$C_{3-8}$ cycloalkyl" as used throughout the present specification refers to cyclic alkyl of 3 to 8 carbons, and as specific examples there may be mentioned cyclopropyl, cyclobutyl, cyclopentyl and cyclohexyl, with cyclopropyl being preferred.

The term "$C_{1-6}$ alkoxy" as used throughout the present specification refers to a substituent wherein the aforementioned "$C_{1-6}$ alkyl" is bonded to oxygen, and as specific examples there may be mentioned methoxy, ethoxy, n-propoxy, i-propoxy, n-butoxy, i-butoxy, sec-butoxy, t-butoxy, n-pentyloxy, i-pentyloxy, sec-pentyloxy, t-pentyloxy, neopentyloxy, 1-methylbutoxy, 2-methylbutoxy, 1,1-dimethylpropoxy, 1,2-dimethylpropoxy, n-hexyloxy, i-hexyloxy, 1-methylpentyloxy, 2-methylpentyloxy, 3-methylpentyloxy, 1,1-dimethylbutoxy, 1,2-dimethylbutoxy, 2,2-dimethylbutoxy, 1,3-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, preferably methoxy, ethoxy, n-propoxy, i-propoxy, n-butoxy, i-butoxy, sec-butoxy, t-butoxy, n-pentyloxy, i-pentyloxy, sec-pentyloxy, t-pentyloxy, neopentyloxy, 1-methylbutoxy, 2-methylbutoxy, 1,1-dimethylpropoxy, 1,2-dimethylpropoxy, n-hexyloxy and i-hexyloxy, more preferably methoxy, ethoxy, n-propoxy, i-propoxy, n-butoxy, i-butoxy, sec-butoxy, t-butoxy, n-pentyloxy, i-pentyloxy, sec-pentyloxy, t-pentyloxy, neopentyloxy, 1-methylbutoxy, 2-methylbutoxy, 1,1-dimethylpropoxy and 1,2-dimethylpropoxy, even more preferably methoxy, ethoxy, n-propoxy, i-propoxy, n-butoxy, i-butoxy, sec-butoxy and t-butoxy, and most preferably methoxy, ethoxy, n-propoxy and i-propoxy.

The term "$C_{3-8}$ cycloalkoxy" as used throughout the present specification refers to cyclic alkoxy of 3 to 8 carbons, and as specific examples there may be mentioned cyclopropoxy, cyclobutoxy, cyclopentyloxy and cyclohexyloxy, with cyclopropoxy being preferred.

A compound represented by the general formula (I) can be produced by the method described in WO02/32872.

Throughout the present specification, the term "pharmacologically acceptable salt" is not particularly restrictive on the type of salt, and as examples of such salts there may be mentioned inorganic acid addition salts such as hydrochloride, sulfate, carbonate, bicarbonate, hydrobromide and hydroiodide; organic carboxylic acid addition salts such as acetate, maleate, lactate, tartarate and trifluoroacetate; organic sulfonic acid addition salts such as methanesulfonate, hydroxymethanesulfonate, hydroxyethanesulfonate, benzenesulfonate, toluenesulfonate and taurine salts; amine addition salts such as trimethylamine salts, triethylamine salts, pyridine salts, procaine salts, picoline salts, dicyclohexylamine salts, N,N'-dibenzylethylenediamine salts, N-methylglucamine salts, diethanolamine salts, triethanolamine salts, tris (hydroxymethylamino)methane salts and phenethylbenzylamine salts; and amino acid addition salts such as arginine salts, lysine salts, serine salts, glycine salts, aspartate and glutamate.

The dosage of a medicine according to the invention will differ depending on the severity of symptoms, patient age, gender and weight, administration form and type of disease, but administration may usually be from 100 μg to 10 g per day for adults, either at once or in divided doses.

There are no particular restrictions on the form of administration of a medicine according to the invention, and it may usually be administered orally or parenterally by conventional methods.

Common excipients, binders, glossy agents, coloring agents, taste correctors and the like, and if necessary stabilizers, emulsifiers, absorption promoters, surfactants and the like, may also be used for formulation, with inclusion of components ordinarily used as starting materials for formulation of pharmaceutical preparations by common methods.

Examples of such components which may be used include animal and vegetable oils (soybean oil, beef tallow, synthetic glycerides, etc.), hydrocarbons (liquid paraffin, squalane, solid paraffin, etc.), ester oils (octyldodecyl myristate, isopropyl myristate, etc.), higher alcohols (cetostearyl alcohol, behenyl alcohol, etc.), silicone resins, silicone oils, surfactants (polyoxyethylene fatty acid esters, sorbitan fatty acid esters, glycerin fatty acid esters, polyoxyethylenesorbitan fatty acid esters, polyoxyethylene hydrogenated castor oil, polyoxyethylenepolyoxypropylene block copolymer, etc.), water-soluble polymers (hydroxyethyl cellulose, polyacrylic acid, carboxyvinyl polymer, polyethyleneglycol, polyvinylpyrrolidone, methyl cellulose, etc.), alcohols (ethanol, isopropanol, etc.), polyhydric alcohols (glycerin, propyleneglycol, dipropyleneglycol, sorbitol, etc.), sugars (glucose, sucrose, etc.), inorganic powders (silicic anhydride, aluminium magnesium silicate, aluminium silicate, etc.), purified water and the like. For pH adjustment there may be used inorganic acids (hydrochloric acid, phosphoric acid, etc.), alkali metal salts of inorganic acids (sodium phosphate, etc.), inorganic bases (sodium hydroxide, etc.), organic acids (lower fatty acids, citric acid, lactic acid, etc.), alkali metal salts of organic acids (sodium citrate, sodium lactate, etc.), and organic bases (arginine, ethanolamine, etc.). If necessary, preservatives, antioxidants and the like may also be added.

EXAMPLES

The present invention will be explained through the following examples, but these examples are in no way limitative on the invention.

Example 1

Effect on Cell Proliferation Stimulated by SCF

Compounds 1, 2, 3 and 4 were tested for their effects on the proliferation of the small cell lung cancer cell line H-526 expressing c-Kit kinase (purchased from ATCC: CRL-5811).

Compound 1: 4-(3-Chloro-4-(cyclopropylaminocarbonyl) aminophenoxy)-7-methoxy-6-quinolinecarboxamide Compound 2: 4-(3-Chloro-4-(ethylaminocarbonyl)aminophenoxy)-7-methoxy-6-quinolinecarboxamide Compound 3: N6-Methoxy-4-(3-chloro-4-(((cyclopropylamino)carbonyl)amino)phenoxy)-7-methoxy-6-quinolinecarboxamide Compound 4: N6-Methoxy-4-(3-chloro-4-(((ethylamino) carbonyl)amino)phenoxy)-7-methoxy-6-quinolinecarboxamide The structures of Compound 1 to 4 are shown below.

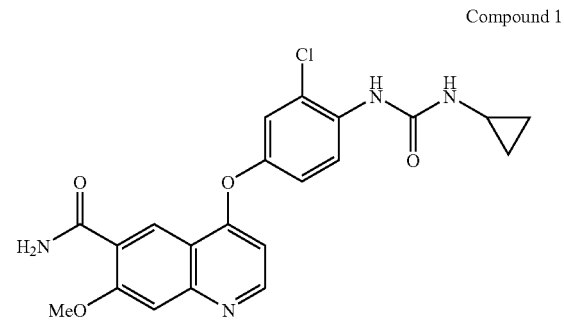

Compound 1

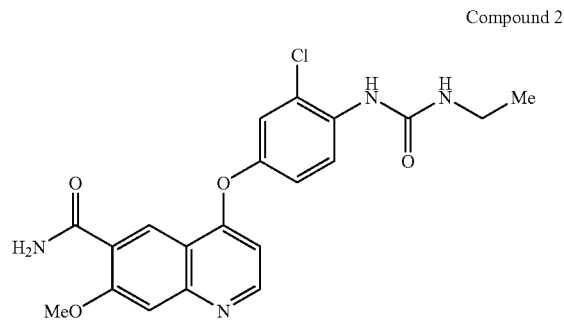

Compound 2

-continued

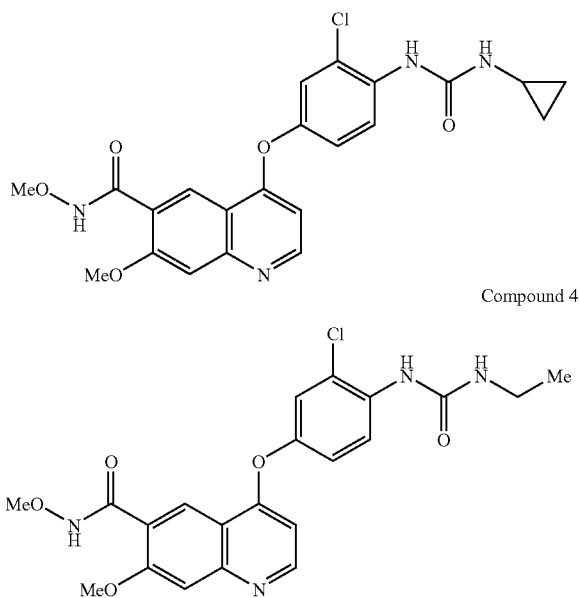

Compound 3

Compound 4

Compound 1 was prepared by the method described in Example 368 of WO02/32872. Compound 2 was prepared by the method described in Example 583 of WO02/32872. Compound 3 was prepared by the method described in Example 417 of WO02/32872. Compound 4 was prepared by the method described in Example 702 of WO02/32872.

H-526 cells were cultured in a 5% $CO_2$ incubator (37° C.) using an RPMI1640 medium (Nissui Pharmaceutical Co., Ltd.) containing 10% FCS (purchased from Cell Culture Technologies). After culturing, H-526 cells were washed with PBS three times and were suspended in an RPMI1640 medium containing 0.1% BSA (Sigma Corporation) (hereinafter abbreviated as "BSA-RPMI1640") at $1.0 \times 10^5$ cells/ml. Each 50 µl of this cell suspension was inoculated to each well of a round bottom 96-well plate, and the suspension was cultured in a 5% $CO_2$ incubator (37° C.) overnight. After culturing overnight, 50 µl of BSA-RPMI1640 containing 200 ng/ml SCF (R&D Co., Ltd.) and 100 µl of BSA-RPMI1640 containing a diluted test substance were added to each well.

On the 7th day after addition of the test substance, 20 µl of Cell Counting Kit-8 (Dojin Laboratories) was added to the well and was cultured in a 5% $CO_2$ incubator (37° C.) for about 2 hours. After color development, the absorbance of each well was determined using a MTP-32 plate reader (Colona Electric Co., Ltd.) at a measuring wavelength of 450 nm and at a reference wavelength of 660 nm. The absorbance of each well was subtracted by the absorbance of the well without addition of SCF, and then the ratio of the absorbance of the well with addition of the test substance to the ratio of the absorbance of the well without addition of the test substance was determined. This ratio was used to calculate the concentration of the test substance required for 50% inhibition of the cell proliferation ($IC_{50}$).

Consequently, Compounds 1, 2, 3 and 4 inhibited the cell proliferation stimulated by SCF as shown in the table below, and these compounds were considered to possess c-Kit kinase inhibitory activity. The $IC_{50}$ of the compound KRN633, which is described in Kazuo Kubo et al., 22nd Symposium on Medicinal Chemistry, Abstracts, pp. 275-277, 2P-320, 2002, proved to be 301 nM and the compound showed only weak activity as compared to Compounds 1, 2, 3 and 4. STI571 known as a c-Kit kinase inhibitor showed $IC_{50}$ of 190 nM.

TABLE 1

| Compound | $IC_{50}$ (nM) |
|---|---|
| Compound 1 | 9.36 |
| Compound 2 | 12.8 |
| Compound 3 | 214 |
| Compound 4 | 56.3 |

Example 2

Effect of Compound 1 on c-Kit Kinase Phosphorylation by SCF Stimulation

Compound 1 was tested for its effect on the phosphorylation of the c-Kit kinase molecule by SCF stimulation in the small cell lung cancer cell line H-526 expressing c-Kit kinase.

H-526 cells were cultured in a 5% $CO_2$ incubator (37° C.) using an RPMI1640 medium containing 10% FCS. After culturing, H-526 cells were washed with PBS three times and were suspended in a BSA-RPMI1640 medium at $5.0 \times 10^5$ cells/ml. Each 1 ml of this cell suspension was inoculated to the well of a 24-well plate and the suspension was cultured in a 5% $CO_2$ incubator (37° C.) for 6 hours. After 6-hours culturing, 1 ml of BSA-RPMI1640 containing a diluted test substance was added to each well and culturing was carried out in a 5% $CO_2$ incubator (37° C.) for 1 hour. Additional culturing was then carried out in a 5% $CO_2$ incubator (37° C.) for 5 minutes after the addition of 10 µl of SCF (10 µg/ml, R&D Corporation). After 5-minutes culturing, the cells were washed with PBS and 100 µl of SDS sample loading buffer was added to the cells to prepare a cell lysate sample. After the sample was heat-treated at 94° C. for 10 minutes, it was cryopreserved at −20° C.

The cell lysate sample, 20 µl, was then electrophoresed on a 4-20% gradient polyacrylamide gel (Daiichi Pure Chemicals Co., Ltd.). After electrophoresis, the sample was transferred to a PVDF membrane (Amersham Pharmacia Biotech Inc.) for 3 hours. The transferred membrane was subjected to immunoblot using a phospho-c-kit (Tyr719) antibody (Cell Signaling Technology Inc.) as a primary antibody and an anti-rabbit IgG, HRP-linked antibody (Cell Signaling Technology Inc.) as a secondary antibody. After the membrane was washed, it was developed with a Super Signal (Pierce Biotechnology, Inc.).

As the results are shown in FIG. 1, c-kit kinase was not phosphorylated (the farthest left lane) in the absence of SCF, and the addition of Compound 1 suppressed the c-Kit kinase phosphorylation that would take place in the presence of SCF in a concentration-dependent manner. The phosphorylation inhibitory activity of STI571, which is known as a c-Kit kinase inhibitor, was approximately one tenth of that of Compound 1.

Example 3

Effect of Compound 1 on Growth of H-526 Tumor Transplanted to Nude Mice

H-526 cells were cultured in a 5% $CO_2$ incubator (37° C.) using an RPMI1640 medium containing 10% FCS. After the culture medium was collected, H-526 cells were washed with PBS twice and were suspended in PBS at $5.0 \times 10^7$ cells/ml.

This cell suspension (0.1 ml) was transplanted to the subcutaneous parts of the right flank of 6-week female Balb/c nu/nu mice (purchased from Charles River Laboratories, Inc.). After transplantation, administration of a test substance was started at the point the tumor volume reached approximately 150 mm$^3$, and thus, oral administration was conducted twice daily for a period of 14 days. The test substance was suspended in a 0.5% methylcellulose solution (Wako Pure Chemical Industries Co., Ltd.) so as to give a dose of 0.1 ml/10 g body weight.

The tumor volume was measured with a caliper twice weekly during the administration period. The long and short diameters of the tumor were measured with a caliper and the tumor volume was calculated according to the equation: ½× long diameter×short diameter×short diameter. Here, the experiment was conducted in a vehicle control group of 10 animals (solvent-administered group) as well as in a test substance administered group of 5 animals.

Figure 2:
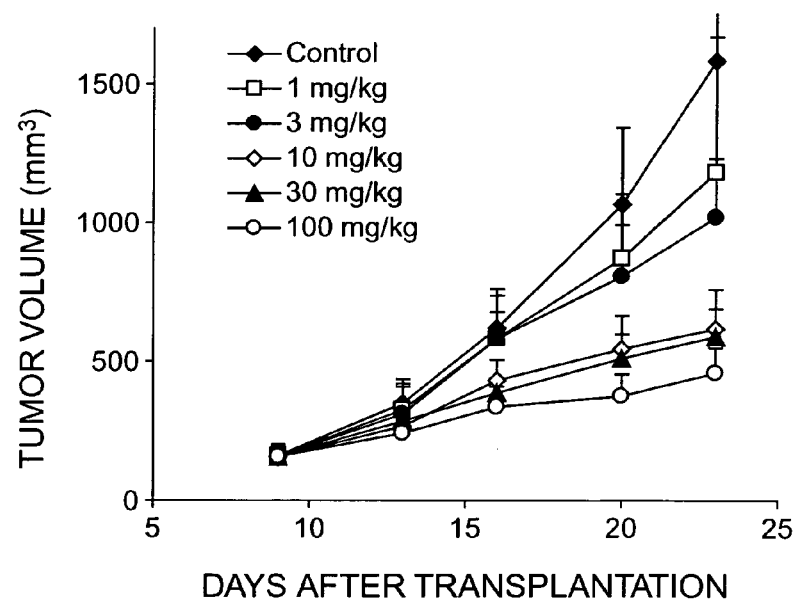
FIG. 2 is a graph showing the relationship between the numbers of days elapsed after transplantation and tumor volume when H-526 was transplanted to a nude mouse.

As the results are shown in FIG. 2, Compound 1 suppressed the growth of the nude mouse transplanted H-526 tumor in a dose-dependent manner. On the other hand, STI571 known as a c-Kit kinase inhibitor showed little anti-tumor effect when administered even at 160 mg/kg.

Example 4

Effect of Compound 1 on c-Kit Kinase Phosphorylation in H-526 Tumor Transplanted to Nude Mice 0.1 ml of a H-526 cell suspension prepared at a concentration of 5.0×10$^7$ cells/ml, was transplanted to the subcutaneous parts of the right latus of 6-week female Balb/c nu/nu mice (purchased from Charles River Laboratories, Inc.). The animals were then divided into a vehicle control group (solvent-administered group) and a test substance administered group at the point the tumor volume reached 300-1000 mm$^3$: the test substance was administered to the latter group. The extracted tumor was placed in a cell lysate buffer (50 mM HEPES (pH 7.4), 150 mM NaCl, 10% glycerol, 1% Triton X-100, 1.5 mm MgCl$_2$, 1 mM EDTA, 100 mM NaF, 1 mM PMSF, 10 µg/ml aprotinin, 50 µg/ml leupeptin, 1 µg/ml peptatin A, 1 mM Na$_3$VO$_4$, 25 mM β-glycerophosphate, and phosphatase inhibitor cocktail II) and homogenized. After centrifugation, the supernatant was protein quantified, and a 3×SDS sample loading buffer was added to prepare a cell lysate sample. Subsequently, the cell lysate was heat-treated at 94° C. for 10 minutes and cryopreserved at −20° C.

The cell lysate sample which was equivalent to 30 µg of protein was electrophoresed on a 4-20% gradient polyacrylamide gel (Daiichi Pure Chemicals Co., Ltd.). After electrophoresis, the sample was transferred to a PVDF membrane (Amersham Pharmacia Biotech Inc.) for 3 hours. In order to assay phosphorylated c-Kit, c-Kit and β-actin, immunoblot was performed using a phospho-c-kit (Tyr719) antibody (Cell Signaling Technologies, Inc.), an anti c-Kit antibody (Cell Signaling Technologies, Inc.) and an anti β-actin antibody (Sigma) as a primary antibody and an anti-rabbit IgG, HRP-linked antibody (Cell Signaling Technologies, Inc.) as a secondary antibody. After the membrane was washed, it was developed with a Super Signal (Pierce Biotechnology, Inc.).

Figure 3:
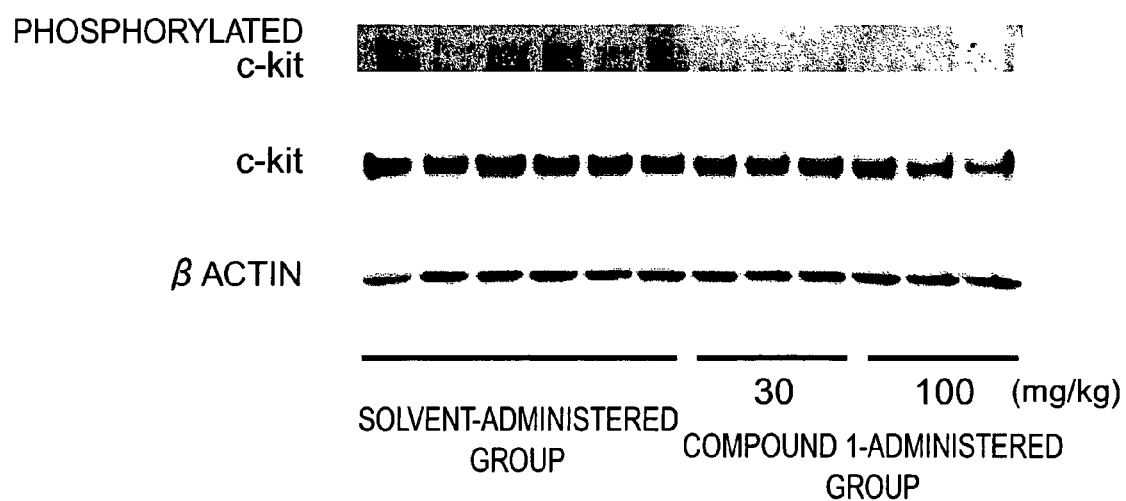
FIG. 3 is a graph showing the result of immunoblot of phosphorylated c-Kit kinase, c-Kit kinase and β-actin when H-526 was transplanted to a nude mouse.

As the results are shown in FIG. 3, Compound 1 reduced phosphorylated c-Kit in tumor tissue when administered at 30 or 100 mg/kg, but c-Kit and β-actin remained unchanged. While Compound 1 completely inhibited phosphorylation when administered at 30 or 100 mg/kg, STI571 known as a c-Kit kinase inhibitor partially inhibited phosphorylation when administered even at 160 mg/kg.

All these result showed Compound 1 inhibits in vivo phosphorylation of c-Kit, and it is confirmed that Compound 1 inhibits activity of c-Kit kinase in vivo and exhibits anti-tumor activity.

Production methods of Compound 1 (4-(3-Chloro-4-(cyclopropylaminocarbonyl)aminophenoxy)-7-methoxy-6-quinolinecarboxamide) (Reference Example 1 to 3), crystals of methanesulfonate of Compound 1 (Reference Example 4 to 9) and formulation of methanesulfonate of Compound 1 (Reference Example 10) were described below.

Reference Example 1

Production Method (1) of 4-(3-Chloro-4-(cyclopropylaminocarbonyl)aminophenoxy)-7-methoxy-6-quinolinecarboxamide To a solution of phenyl N-(4-(6-carbamoyl-7-methoxy-4-quinolyl)oxy-2-chlorophenyl)carbamate (described in WO02/32872; 17.5 g, 37.7 mmol) dissolved in N,N-dimethylformamide (350 mL), was added cyclopropylamine (6.53 mL, 94.25 mmol) under nitrogen atmosphere, and the mixture were stirred at room temperature overnight. The mixture was poured into water (1.75 L), and stirred. Precipitated crude crystals were filtered off, washed with water, and dried at 70° C. for 50 minutes. Ethanol (300 mL) was added to the crude crystals, the mixture was heated to reflux for about 30 minutes to dissolve the crystals, and gradually cooled to room temperature overnight while stirring. Precipitated crystals were filtered off, dried in vacuo, and dried at 70° C. for 8 hours to give crystals of the title compound (12.91 g, yield 80.2 %).

Reference Example 2

Production Method (2) of 4-(3-Chloro-4-(cyclopropylaminocarbonyl)aminophenoxy)-7-methoxy-6-quinolinecarboxamide (1) production of phenyl N-(2-chloro-4-hydroxyphenyl) carbamate

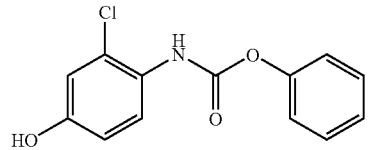

To a suspension of 4-amino-3-chlorophenol (23.7 g) in N,N-dimethylformamide (100 mL) was added pyridine (23.4 mL) while cooling in an ice-water bath, and phenyl chloroformate (23.2 mL) was added dropwise at a temperature not higher than 20° C. After the mixture was stirred at room temperature for 30 minutes, water (400 mL), ethyl acetate (300 mL) and 6N-HCl (48 mL) were added thereto, the mixture was further stirred, and the organic layer was separated off. The organic layer was twice washed with 10% brine (200 mL), and dried over magnesium sulfate. Evaporation of the solvent yielded the title compound (46 g) as a solid.

$^1$H-NMR Spectrum (CDCl$_3$) δ (ppm): 5.12 (1H, br s), 6.75 (1H, dd, J=9.2, 2.8 Hz), 6.92 (1H, d, J=2.8 Hz), 7.18-7.28 (4H, m), 7.37-7.43 (2H, m), 7.94 (1H, br s)

(2) production of phenyl 1-(2-chloro-4-hydroxyphenyl)-3-cyclopropylurea

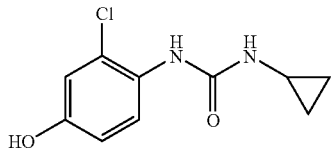

To a solution of phenyl N-(2-chloro-4-hydroxyphenyl)carbamate dissolved in N,N-dimethylformamide (100 mL) was added cyclopropylamine (22.7 mL) while cooling in an ice-water bath, and the mixture was stirred overnight at room temperature. Water (400 mL), ethyl acetate (300 mL) and 6N-HCl (55 mL) were added thereto, the mixture was further stirred, and the organic layer was separated off. The organic layer was twice washed with 10% brine (200 mL), and dried over magnesium sulfate. Evaporation of the solvent yielded prism crystals, the crystals were washed with heptane and filtered off to give the title compound (22.8 g, 77% yield from 4-amino-3-chlorophenol).

$^1$H-NMR Spectrum (CDCl$_3$) δ (ppm): 0.72-0.77 (2H, m), 0.87-0.95 (2H, m), 2.60-2.65 (1H, m), 4.89 (1H, br s), 5.60 (1H, br s), 6.71 (1H, dd, J=8.8, 2.8 Hz), 6.88 (1H, d, J=2.8 Hz), 7.24-7.30 (1H, br s), 7.90 (1H, d, J=8.8 H)

(2) production of 4-(3-Chloro-4-(cyclopropylaminocarbonyl)aminophenoxy)-7-methoxy-6-quinolinecarboxamide TO dimethylsulfoxide (20 mL) were added 7-methoxy-4-chloroquinoline-6-carboxamide (0.983 g), 1-(2-chloro-4-hydroxyphenyl)-3-cyclopropylurea (1.13 g) and cesium carbonate (2.71 g), and the mixture was stirred at 70° C. for 23 hours. The mixture was cooled to room temperature, addition of water (50 mL) yielded crystals, and the crystals were filtered off to give the title compound (1.56 g, yield 88%).

Reference Example 3

Production Method (3) of 4-(3-Chloro-4-(cyclopropylaminocarbonyl)aminophenoxy)-7-methoxy-6-quinolinecarboxamide To a reaction vessel were added 7-mthoxy-4-chloroinoline-6-carboxamide (5.00 kg, 21.13 mol), dimethylsulfoxide (55.05 kg), 1-(2-chloro-4-hydroxyphenyl)-3-cyclopropylurea (5.75 kg, 25.35 mol) and potassium t-butoxide (2.85 kg, 25.35 mol) under nitrogen atmosphere. The mixture was stirred at 20° C. for 30 minutes, and heated to 65° C. over 2.5 hours. The mixture was stirred at the same temperature for 19 hours, and 33% (v/v) acetone-water (5.0 L) and water (10.0 L) were added dropwise over 3.5 hours. After the addition, the mixture was stirred at 60° C. for 2 hours, and 33% (v/v) acetone-water (20.0 L) and water (40.0 L) were added dropwise at a temperature not lower than 55° C. over 1 hour. The mixture was stirred at 40° C. for 16 hours, precipitated crystals were filtered off by a nitrogen pressured filter and washed with 33% (v/v) acetone-water (33.3 L), water (66.7 L) and acetone (50.0 L). Resultant crystals were dried at 60° C. for 22 hours by a conical vacuum drier to give the title compound (7.78 kg, yield 96.3%).

The values of $^1$H-NMR chemical shift of 4-(3-Chloro-4-(cyclopropylaminocarbonyl)aminophenoxy)-7-methoxy-6-quinolinecarboxamide obtained in Reference Examples 1 to 3 corresponded to those described in WO02/32872.

Reference Example 4

Production Method of Crystals (A) of 4-(3-chloro-4-(cyclopropylaminocarbonyl)aminophenoxy)-7-methoxy-6-quinolinecarboxamide methanesulfonate (Method 1) 4-(3-Chloro-4-(cyclopropylaminocarbonyl)aminophenoxy)-7-methoxy-6-quinolinecarboxamide (700 mg, 1.64 mmol) was dissolved in a mixed solution of methanol (14 mL) and methanesulfonic acid (143 µL, 1.97 mmol) at 70° C. After the confirmation of the dissolution of the compound, the mixture was cooled to room temperature over 5.5 hours, stirred at room temperature for 18.5 hours, and crystals were filtered off. The resultant crystals were dried at 60° C. to give the title crystals (647 mg).

(Method 2) 4-(3-Chloro-4-(cyclopropylaminocarbonyl)aminophenoxy)-7-methoxy-6-quinolinecarboxamide (600 mg, 1.41 mmol) was dissolved in a mixed solution of acetic acid (6 mL) and methanesulfonic acid (200 µL, 3.08 mmol) at 50° C. After the confirmation of the dissolution of the compound, to the mixture were added ethanol (7.2 mL) and seed crystals (A) of 4-(3-Chloro-4-(cyclopropylaminocarbonyl)aminophenoxy)-7-methoxy-6-quinolinecarboxamide methanesulfonate (12 mg), and ethanol (4.8 mL) was added dropwise over 2 hours. After the addition, the mixture was stirred at 40° C. for 1 hour and at room temperature for 9 hours, and crystals were filtered off. The resultant crystals were dried at 60° C. to give the title crystals (545 mg).

Reference Example 5

Production Method of Crystals (B) of 4-(3-chloro-4-(cyclopropylaminocarbonyl)aminophenoxy)-7-methoxy-6-quinolinecarboxamide methanesulfonate Crystals (I) of an acetic acid solvate of 4-(3-chloro-4-(cyclopropylaminocarbonyl)aminophenoxy)-7-methoxy-6-quinolinecarboxamide methanesulfonate (250 mg) prepared in Reference Example 9 were dried under aeration at 30° C. for 3 hours and 40° C. for 16 hours to give the title crystals (240 mg).

Reference Example 6

Production Method of Crystals (C) of 4-(3-chloro-4-(cyclopropylaminocarbonyl)aminophenoxy)-7-methoxy-6-quinolinecarboxamide methanesulfonate (Method 1) n-Butyl acetate (12 mL) was added to crystals of a dimethylsulfoxide solvate of 4-(3-chloro-4-(cyclopropylaminocarbonyl)aminophenoxy)-7-methoxy-6-quinolinecarboxamide methanesulfonate (600 mg, 1.15 mmol) prepared in Method 1 of Reference Example 7, the mixture was stirred at 115° C. for 10 hours and at room temperature for 1.5 hours, and crystals were filtered off. Drying under aeration at 60° C. gave the title crystals (503 mg).

(Method 2) Ethanol (6.4 mL) was added to crystals (I) of an acetic acid solvate of 4-(3-chloro-4-(cyclopropylaminocarbonyl)aminophenoxy)-7-methoxy-6-quinolinecarboxamide methanesulfonate (1.28 g) prepared in Reference Example 9, the mixture was dissolved at 40° C., and stirred at the same temperature for 36 hours. Precipitated crystals were filtered off, and dried at 50° C. to give the title crystals (0.87 g).

(Method 3) In a mixed solution of acetic acid (14 mL) and methanesulfonic acid (0.37 mL, 5.62 mmol) were dissolved 4-(3-chloro-4-(cyclopropylaminocarbonyl)aminophenoxy)-7-methoxy-6-quinolinecarboxamide (2.00 g, 4.69 mmol) at 40° C. After the confirmation of the dissolution, to the mixture were added 2-propanol (9 mL) and seed crystals (C) of 4-(3-chloro-4-(cyclopropylaminocarbonyl)aminophenoxy)-7-methoxy-6-quinolinecarboxamide methanesulfonate (100 mg). The mixture was stirred for 20 minutes, isopropyl acetate (10 mL) was added dropwise over 30 minutes. After the addition of isopropyl acetate, the mixture was stirred for 1.5 hours and at 15° C. for 14 hours. Precipitated crystals were filtered off, and dried at 60° C. to give the title crystals (2.22 g).

(Method 4) 4-(3-chloro-4-(cyclopropylaminocarbonyl)aminophenoxy)-7-methoxy-6-quinolinecarboxamide (1.28 g, 3 mmol) and acetic acid (12.8 mL) were mixed, methanesulfonic acid (0.408 mL, 6.3 mmol) was added to this suspension, and the mixture was stirred at room temperature for dissolution. The mixture was heated in a bath at a temperature of 30° C., and 2-propanol was added (7.7 mL). Seed crystals (C) of 4-(3-chloro-4-(cyclopropylaminocarbonyl)aminophenoxy)-7-methoxy-6-quinolinecarboxamide methanesulfonate was added, and 2-propanol (1.28 mL each, 14 times) was added over 44 minutes. After removal of the bath, the mixture was stirred at room temperature for 10 minutes, stirred in a water bath for 5 minutes, and further stirred in the water bath cooled with a little ice for 25 minutes (inner temperature 17.6° C.). The resultant crystals were filtered off, and washed with 2-propanol (10 mL). The resultant crystals after filtration were mixed with ethanol (6.4 mL) and the mixture was stirred at room temperature for 1 hour. The resultant crystals were filtered off, washed with ethanol (4 mL), and dried at 60° C. to give the title crystals (1068 mg).

Reference Example 7

Production Method of Crystals of a dimethylsulfoxide Solvate of 4-(3-chloro-4-(cyclopropylaminocarbonyl)aminophenoxy)-7-methoxy-6-quinolinecarboxamide methanesulfonate (Method 1) Dimethylsulfoxide (7 mL) was added to 4-(3-chloro-4-(cyclopropylaminocarbonyl)aminophenoxy)-7-methoxy-6-quinolinecarboxamide (700 mg, 1.640 mmol), and the compound was dissolved at 80° C. To the mixture were added methanesulfonic acid (143 μL, 1.97 mmol), ethyl acetate (1.4 mL) and seed crystals (A) of 4-(3-chloro-4-(cyclopropylaminocarbonyl)aminophenoxy)-7-methoxy-6-quinolinecarboxamide methanesulfonate at 60° C., and ethyl acetate (5.6 mL) was further added dropwise over 45 minutes. Fifteen minutes after the completion of the addition of ethyl acetate, the mixture was cooled to room temperature over 1 hour, and stirred at the same temperature for 18 hours. Precipitated crystals were filtered off, and dried at 60° C. to give the title crystals (746 mg).

(Method 2) Dimethylsulfoxide (6.8 mL) was added to 4-(3-chloro-4-(cyclopropylaminocarbonyl)aminophenoxy)-7-methoxy-6-quinolinecarboxamide (854 mg, 2 mmol) at room temperature, and the compound was dissolved at 60° C. To the mixture were added methanesulfonic acid (389 μL, 6 mmol) and seed crystals (A) of 4-(3-chloro-4-(cyclopropylaminocarbonyl)aminophenoxy)-7-methoxy-6-quinolinecarboxamide methanesulfonate at the same temperature, and 2-propanol (6.8 mL) was added dropwise over 30 minutes. After the addition of 2-propanol, the mixture was cooled to 15° C. over 2 hours, and stirred at the same temperature for 30 minutes. Precipitated crystals were filtered off, and dried at 60° C. to give the title crystals (1095 mg).

(Method 3) Dimethylsulfoxide (6.8 mL) was added to 4-(3-chloro-4-(cyclopropylaminocarbonyl)aminophenoxy)-7-methoxy-6-quinolinecarboxamide (854 mg, 2 mmol) at room temperature, and the compound was dissolved at 62° C. To the mixture were added methanesulfonic acid (454 μL, 7 mmol) and seed crystals (A) of 4-(3-chloro-4-(cyclopropylaminocarbonyl)aminophenoxy)-7-methoxy-6-quinolinecarboxamide methanesulfonate at the same temperature, and 2-propanol (13.6 mL) was added dropwise over 1 hour. After the addition of 2-propanol, the mixture was cooled to 15° C. over 2 hours, and stirred at the same temperature for 30 minutes. Precipitated crystals were filtered off, and dried at 60° C. to give the title crystals (1082 mg)

Reference Example 8

Production Method of Crystals (F) of a Hydrate of 4-(3-chloro-4-(cyclopropylaminocarbonyl)aminophenoxy)-7-methoxy-6-quinolinecarboxamide methanesulfonate In a mixed solution of acetic acid (1.5 mL) and methanesulfonic acid (31 μL, 0.422 mmol) was dissolved 4-(3-chloro-4-(cyclopropylaminocarbonyl)aminophenoxy)-7-methoxy-6-quinolinecarboxamide (150 mg, 0.351 mmol) at 50° C. After the confirmation of the dissolution, to the mixture were added ethyl acetate (0.6 mL) and seed crystals (A) of 4-(3-chloro-4-(cyclopropylaminocarbonyl)aminophenoxy)-7-methoxy-6-quinolinecarboxamide methanesulfonate prepared in Method 1 of Reference Example 4, and ethyl acetate (1.8 mL) was added dropwise over 2 hours. After the addition of ethyl acetate, the mixture was stirred at 50° C. for 30 minutes, and at room temperature for 7.5 hours. Precipitated crystals were filtered off, and dried at 60° C. to give the title crystals (176 mg).

Reference Example 9

Production Method of Crystals (I) of an Acetic Acid Solvate of 4-(3-chloro-4-(cyclopropylaminocarbonyl)aminophenoxy)-7-methoxy-6-quinolinecarboxamide methanesulfonate In a mixed solution of acetic acid (14 mL) and methanesulfonic acid (0.36 mL, 5.62 mmol) was dissolved 4-(3-chloro-4-(cyclopropylaminocarbonyl)aminophenoxy)-7-methoxy-6-quinolinecarboxamide (2.00 g, 4.69 mmol) at 40° C. After the confirmation of the dissolution, to the mixture were added 1-propanol (4 mL) and seed crystals (C) of 4-(3-chloro-4-(cyclopropylaminocarbonyl)aminophenoxy)-7-methoxy-6-quinolinecarboxamide methanesulfonate (100 mg), and 1-propanol (14 mL) and isopropyl acetate (10 mL) were added dropwise over 1 hour. After the addition, the mixture was stirred at 40° C. for 1 hour and at 25° C. for 40 minutes. Precipitated crystals were filtered off to give the title crystals (2.61 g).

$^1$H-NMR chemical shift of the methanesulfonate is as follow.

$^1$H-NMR Spectrum (DMSO-$d_6$) δ (ppm): 0.44 (2H, m), 0.67 (2H, m), 2.36 (3H, s), 2.59 (1H, m), 4.09 (3H, s), 6.95 (1H, d, J=7 Hz), 7.25 (1H, d, J=2 Hz), 7.36 (1H, dd, J=3, 9 Hz), 7.63 (1H, d, J=3 Hz), 7.65 (1H, s), 7.88 (1H, brs), 7.95 (1H, brs), 8.06 (1H, s), 8.37 (1H, d, J=9 Hz), 8.73 (1H, s), 8.97 (1H, d, J=7 Hz)

Reference Example 10

Formulation of 4-(3-Chloro-4-(cyclopropylaminocarbonyl)aminophenoxy)-7-methoxy-6-quinolinecarboxamide methanesulfonate Based on the prescription described in Table 2, 0.1 mg tablet was produced by the following method 1, and 1 mg tablet and 10 mg tablet were produced by the following method 2.

(Method 1) After mixing D-mannitol, crystalline cellulose and hydroxypropylcellulose, a major ingredient dispersed in an appropriate amount of ethanol added to the mixture for granulation. The granulated product was dried and then size-controlled. Sodium croscarmellose and sodium stearyl fumarate were added to the resultant granule and mixed, then were subjected to tableting. The resultant tablets were film coated with a mobile layer using a mixture of coating base.

(Method 2) After mixing a major ingredient and light anhydrous silicic acid, D-mannitol, crystalline cellulose and hydroxypropylcellulose were further added and mixed. An appropriate amount of ethanol was added for granulation. The granulated product was dried and then size-controlled. Sodium croscarmellose and sodium stearyl fumarate were added to the resultant granule and mixed, then were subjected to tableting. The resultant tablets were film coated with a mobile layer using a mixture of coating base.

TABLE 2

| Material | Purpose | 0.1 mg tablet | 1 mg tablet | 10 mg tablet |
|---|---|---|---|---|
| compound[*1] | major ingredient | 0.1 | 1 | 10 |
| light anhydrous silicic acid | excipient | 0 | 8 | 32 |
| D-mannitol | excipients | 60.4 | 51.5 | 200 |
| crystalline cellulose | excipients | 30 | 30 | 120 |
| hydroxypropylcellulose | binder | 3 | 3 | 12 |
| sodium croscarmellose | disintegrator | 5 | 5 | 20 |
| sodium stearyl fumarate | lubricant | 1.5 | 1.5 | 6 |
| a mixture of coating base[*2] | coating agent | 5 | 5 | 11 |
| total | | 105 | 105 | 411 |

[*1] 4-(3-Chloro-4-(cyclopropylaminocarbonyl)aminophenoxy)-7-methoxy-6-quinolinecarboxamide methanesulfonate
[*2] a pre-mixed material consisting of 56.0% hydroxypropylmethylcellulose, 28.0% talc, 10.0% Macrogol 6000, 4.0% titanium oxide and 2.0% yellow iron sesquioxide (w/w %).

It was discovered that a compound represented by the general formula (I) shows a strong c-Kit kinase inhibitory activity, and it inhibits proliferation of c-Kit kinase activated-cancer cells both in vitro and in vivo. Therefore, the compound represented by the general formula (I) is shown to be applicable as an anti-cancer agent for cancers malignant-transformed by activation of c-Kit kinase. Moreover, a c-Kit kinase inhibitor comprising as an active ingredient the compound represented by the general formula (I) is suggest to be effective for diseases such as mastocytosis, allergy and asthma, which are considered to be caused by c-Kit kinase.

What is claimed is:

1. A method for treating a cancer that express c-kit in a patient, comprising:
    a) determining if the patient's cancer expresses c-Kit kinase or a mutant c-Kit kinase; and
    b) if the cancer is determined to express c-Kit kinase or a mutant c-Kit kinase, administering to the patient a pharmacologically effective dose to inhibit c-Kit activity of said cKit kinase or mutant c-Kit kinase of a compound selected from the group consisting of:
    4-(3-chloro-4-(cyclopropylaminocarbonyl)aminophenoxy)-7-methoxy-6-quinolinecarboxamide;
    4-(3-chloro-4-(ethylaminocarbonyl)aminophenoxy)-7-methoxy-6-quinolinecarboxamide,
    N6-methoxy-4-(3-chloro-4-(((cyclopropylamino)carbonyl)amino)phenoxy)-7-methoxy-6-quinolinecarboxamide; and
    N6-methoxy-4-(3-chloro-4-(((ethylamino)carbonyl)amino)phenoxy)-7-methoxy-6-quinolinecarboxamide, or a pharmaceutically acceptable salt thereof.

2. The method of claim 1, wherein the cancer is acute myelogenous leukemia, a small cell lung cancer, or gastorintestinal stromal tumor (GIST).

3. A method for treating mastocytosis, allergy, or asthma comprising administering to a patient suffering from one or more of the diseases a pharmacologically effective dose to inhibit c-Kit activity of said cKit kinase or mutant c-Kit kinase of a compound selected from the group consisting of:
    4-(3-chloro-4-(cyclopropylaminocarbonyl)aminophenoxy)-7-methoxy-6-quinolinecarboxamide;
    4-(3-chloro-4-(ethylaminocarbonyl)aminophenoxy)-7-methoxy-6-quinolinecarboxamide,
    N6-methoxy-4-(3-chloro-4-(((cyclopropylamino)carbonyl)amino)phenoxy)-7-methoxy-6-quinolinecarboxamide; and
    N6-methoxy-4-(3-chloro-4-(((ethylamino)carbonyl)amino)phenoxy)-7-methoxy-6-quinolinecarboxamide, or a pharmaceutically acceptable salt thereof:

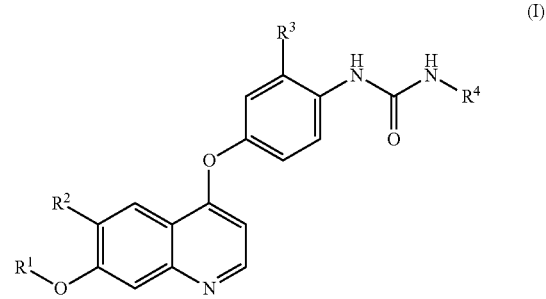

(I)

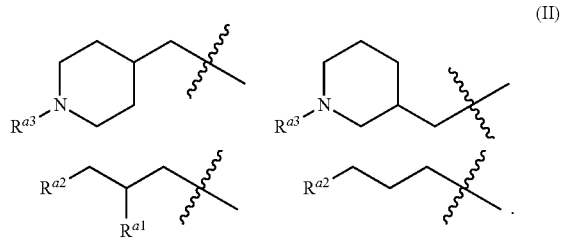

(II)

4. A method of inhibiting c-kit activity in a cancer cell in a patient comprising:
    a) determining if a cell expresses c-Kit kinase or a mutant c-Kit kinase; and
    b) if the cell is determined to express c-Kit kinase or a mutant c-Kit kinase, applying to the cell a pharmacologically effective dose to inhibit c-Kit activity of said cKit kinase or mutant c-Kit kinase of a compound selected from the group consisting of:
    4-(3-chloro-4-(cyclopropylaminocarbonyl)aminophenoxy)-7-methoxy-6-quinolinecarboxamide;
    4-(3-chloro-4-(ethylaminocarbonyl)aminophenoxy)-7-methoxy-6-quinolinecarboxamide, N6-methoxy-4-

(3-chloro-4-(((cyclopropylamino)carbonyl)amino) phenoxy)-7-methoxy-6-quinolinecarboxamide; and N6-methoxy-4-(3-chloro-4-(((ethylamino)carbonyl) amino)phenoxy)-7-methoxy-6-quinolinecarboxamide, or a pharmaceutically acceptable salt thereof.

5. The method of claim 1 or 4 wherein the compound is 4-(3-chloro-4-(cyclopropylaminocarbonyl)aminophenoxy)-7-methoxy-6-quinolinecarboxamide or a pharmaceutically acceptable salt thereof.

6. The method of claim 1 or 4, wherein the compound) is 4-(3-chloro-4-(cyclopropylaminocarbonyl)aminophenoxy)-7-methoxy-6-quinolinecarboxamide.

7. The method of claim 1, wherein the cancer is mast cell leukemia, testicular cancer, ovarian cancer, breast cancer, brain cancer, neuroblastoma, or colorectal cancer.

8. The method of claim 1, wherein the c-Kit kinase or mutant c-Kit kinase is activated.

9. The method of claim 1, wherein the c-Kit kinase or mutant c-Kit kinase is phosphorylated.

10. The method of claim 1, wherein the expression of c-Kit kinase or mutant c-Kit kinase is excessive.

11. The method of claim 1, wherein the determining step comprises extracting cells from the patient.

12. The method of claim 11, wherein the extracted cells comprise cancer cells.

13. The method of claim 4, wherein the cancer cell is a mast cell leukemia, testicular cancer, ovarian cancer, breast cancer, brain cancer, neuroblastoma, or colorectal cancer cell.

14. The method of claim 4, wherein the cancer cell is a myelogenous leukemia, a small cell lung cancer or a GIST cancer cell.

15. The method of claim 1, wherein the compound is administered orally or parenterally.

16. The method of claim 4, wherein the c-Kit kinase or mutant c-Kit kinase is activated.

17. The method of claim 4, wherein the c-Kit kinase or mutant c-Kit kinase is phosphorylated.

18. The method of claim 4, wherein the expression of c-Kit kinase or mutant c-Kit kinase is excessive.

19. The method of claim 4, wherein the determining step comprises extracting cells from the patient.

20. The method of claim 1, wherein the compound is administered orally or parenterally.

21. The method of claim 1, wherein the cancer is determined to express a mutant c-Kit kinase.

22. The method of claim 4, wherein the cell is determined to express a mutant c-Kit kinase.

* * * * *

UNITED STATES PATENT AND TRADEMARK OFFICE
CERTIFICATE OF CORRECTION

| | | |
|---|---|---|
| PATENT NO. | : 7,994,159 B2 | |
| APPLICATION NO. | : 10/797903 | |
| DATED | : August 9, 2011 | |
| INVENTOR(S) | : Yuji Yamamoto et al. | |

It is certified that error appears in the above-identified patent and that said Letters Patent is hereby corrected as shown below:

Column 18, line 1 (Claim 1), please delete "cKit" and insert -- c-Kit --, therefor;

Column 18, line 6 (Claim 1), please delete "quinolinecarboxamide," and insert -- quinolinecarboxamide; --, therefor;

Column 18, lines 14-15 (Claim 2), please delete "gastorintestinal" and insert -- gastrointestinal --, therefor;

Column 18, lines 16-54 (Claim 3), please delete claim 3.

Column 18, line 62 (Claim 4), please delete "cKit" and insert -- c-Kit --, therefor;

Column 18-19, lines 55-67 and lines 1-5 please delete "4. A method of inhibiting c-kit activity in a cancer cell in a patient comprising:
a) determining if a cell expresses c-Kit kinase or a mutant c-Kit kinase; and
b) if the cell is determined to express c-Kit kinase or a mutant c-Kit kinase, applying to the cell
a pharmacologically effective dose to inhibit c-Kit activity of said cKit kinase or mutant c-Kit kinase of a compound selected from the group consisting of:
4-(3-chloro-4- (cyclopropylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxarnide,
N6- methoxy-4-(3-chloro-4-(((cyclopropylamino)carbonyl)amino)phenoxy)-7-methoxy-6-quinolinecarboxamide; and
N6-methoxy-4-(3-chloro-4-(((ethylamino)carbonyl)amino)phenoxy)-7-methoxy-6-quinolinecarboxamide, or a pharmaceutically acceptable salt thereof."
and insert -- 4. A method of inhibiting c-kit activity in a cancer cell in a patient comprising:
a) determining if a cell expresses c-Kit kinase or a mutant c-Kit kinase; and
b) if the cell is determined to express c-Kit kinase or a mutant c-Kit kinase, applying to the cell Signed and Sealed this
Thirteenth Day of March, 2012

David J. Kappos
*Director of the United States Patent and Trademark Office*

CERTIFICATE OF CORRECTION (continued)
U.S. Pat. No. 7,994,159 B2 a pharmacologically effective dose to inhibit c-Kit activity of said c-Kit kinase or mutant c-Kit kinase of a compound selected from the group consisting of:
4-(3-chloro-4- (cyclopropylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxamide;
N6- methoxy-4-(3-chloro-4-(((cyclopropylamino)carbonyl)amino)phenoxy)-7-methoxy-
                6-quinolinecarboxamide; and
N6-methoxy-4-(3-chloro-4-(((ethylamino)carbonyl)amino)phenoxy)-7-methoxy-
6-quinolinecarboxamide, or a pharmaceutically acceptable salt thereof. --, therefor.

Column 19, line 10 (Claim 6), please delete "compound)" and insert -- compound --, therefor.